United States Patent
Dilorenzo et al.

(10) Patent No.: US 9,670,451 B2
(45) Date of Patent: Jun. 6, 2017

(54) METHODS AND SYSTEMS OF GROWING AND HARVESTING CELLS IN A HOLLOW FIBER BIOREACTOR SYSTEM WITH CONTROL CONDITIONS

(71) Applicant: Terumo BCT, Inc., Lakewood, CO (US)

(72) Inventors: Thomas G. Dilorenzo, Arvada, CO (US); Edward Allan Stanton, IV, Lakewood, CO (US); Glen Delbert Antwiler, Lakewood, CO (US); Michael E. Kinzie, Lafayette, CO (US); Brian J. Nankervis, Thornton, CO (US); Monique Givens, Westminster, CO (US); Casey V. Medina, Westminster, CO (US); Jon A. Dodd, Littleton, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

(21) Appl. No.: 14/548,617

(22) Filed: Nov. 20, 2014

(65) Prior Publication Data

US 2015/0079664 A1    Mar. 19, 2015

Related U.S. Application Data

(62) Division of application No. 13/269,512, filed on Oct. 7, 2011, now Pat. No. 8,895,291.

(Continued)

(51) Int. Cl.
*C12M 1/34* (2006.01)
*C12M 3/00* (2006.01)

(Continued)

(52) U.S. Cl.
CPC ............ *C12M 41/44* (2013.01); *C12M 23/42* (2013.01); *C12M 23/44* (2013.01); *C12M 25/10* (2013.01);

(Continued)

(58) Field of Classification Search
CPC ...... C12M 23/42; C12M 25/10; C12M 25/12; C12M 29/16; C12M 29/20; C12M 41/44; C12M 41/48; G06F 8/38

(Continued)

(56) References Cited

U.S. PATENT DOCUMENTS 4,231,366 A    11/1980   Schael
4,388,944 A     6/1983   Honma et al.

(Continued)

FOREIGN PATENT DOCUMENTS

WO    97/014962 A1    4/1997
WO    99/057561 A2   11/1999

(Continued)

OTHER PUBLICATIONS

International Search Report and Written Opinion, PCT/US2009/062213, Feb. 3, 2010.

(Continued)

*Primary Examiner* — Nathan Bowers
*Assistant Examiner* — Lydia Edwards
(74) *Attorney, Agent, or Firm* — Elizabeth J. Reagan; René A. Pereyra; John R. Merkling

(57) ABSTRACT

Embodiments described herein generally relate to methods and systems for using an air removal chamber as a control for a process in a cell expansion system. The air removal chamber may be mounted on a fluid conveyance assembly for use with the system. Fluid is pumped into a fluid containment chamber of the air removal chamber, in which the level of fluid in the fluid containment chamber may be (Continued)

monitored through the use of one or more sensors. The sensors are capable of detecting air, a lack of fluid, fluid, and/or a gas/fluid interface, e.g., an air/fluid interface, at measuring positions within the air removal chamber. Protocols for use with the system may include one or more stop conditions. In an embodiment, the stopping of a process is automated based on the detection of air, a lack of fluid, and/or a gas/fluid interface in the air removal chamber.

8 Claims, 6 Drawing Sheets

Related U.S. Application Data

(60) Provisional application No. 61/391,152, filed on Oct. 8, 2010, provisional application No. 61/434,726, filed on Jan. 20, 2011.

(51) Int. Cl.
*C12M 1/12* (2006.01)
*C12M 1/00* (2006.01)
*C12M 1/36* (2006.01)
*G06F 9/44* (2006.01)

(52) U.S. Cl.
CPC ............ *C12M 25/12* (2013.01); *C12M 29/16* (2013.01); *C12M 29/20* (2013.01); *C12M 41/48* (2013.01); *G06F 8/38* (2013.01)

(58) Field of Classification Search
USPC ........................................... 435/283.1–309.4
See application file for complete search history.

(56) References Cited

U.S. PATENT DOCUMENTS

| | | | |
|---|---|---|---|
| 4,436,620 A | 3/1984 | Bellotti et al. | |
| 4,798,090 A | 1/1989 | Heath et al. | |
| 4,918,019 A | 4/1990 | Guinn | |
| 4,976,708 A | 12/1990 | Oshiyama | |
| 4,997,464 A | 3/1991 | Kopf | |
| 5,026,650 A | 6/1991 | Schwarz et al. | |
| 5,126,238 A | 6/1992 | Gebhard et al. | |
| 5,153,133 A | 10/1992 | Schwarz et al. | |
| 5,162,225 A | 11/1992 | Sager et al. | |
| 5,178,603 A | 1/1993 | Prince | |
| 5,202,254 A | 4/1993 | Amiot et al. | |
| 5,316,905 A | 5/1994 | Mori et al. | |
| 5,424,209 A | 6/1995 | Kearney | |
| 5,958,763 A | 9/1999 | Goffe | |
| 5,985,653 A | 11/1999 | Armstrong et al. | |
| 6,001,585 A | 12/1999 | Gramer | |
| 6,048,721 A | 4/2000 | Armstrong et al. | |
| 6,096,532 A | 8/2000 | Armstrong et al. | |
| 6,228,635 B1 | 5/2001 | Armstrong et al. | |
| 6,238,908 B1 | 5/2001 | Armstrong et al. | |
| 6,604,555 B2 | 8/2003 | Blatt et al. | |
| 7,270,996 B2 * | 9/2007 | Cannon et al. | 435/293.1 |
| 7,855,070 B2 | 12/2010 | Vukasinovic et al. | |
| 7,892,332 B2 | 2/2011 | Prisco et al. | |
| 7,998,725 B2 | 8/2011 | Schein et al. | |
| 8,109,284 B2 | 2/2012 | Furey et al. | |
| 8,128,740 B2 | 3/2012 | Wright et al. | |
| 8,309,347 B2 | 11/2012 | Antwiler | |
| 8,895,291 B2 | 11/2014 | DiLorenzo et al. | |
| 8,999,046 B2 | 4/2015 | Dilorenzo et al. | |
| 9,284,523 B2 | 3/2016 | Dodd et al. | |
| 2003/0037836 A1* | 2/2003 | Blatt et al. | 141/21 |
| 2004/0221719 A1* | 11/2004 | Wright et al. | 95/241 |
| 2005/0239198 A1 | 10/2005 | Kunas et al. | |
| 2006/0137663 A1 | 6/2006 | Vaught | |
| 2008/0032398 A1 | 2/2008 | Cannon et al. | |
| 2008/0145925 A1 | 6/2008 | Sakai et al. | |
| 2010/0105138 A1 | 4/2010 | Dodd et al. | |
| 2011/0155256 A1 | 6/2011 | DiLorenzo et al. | |

FOREIGN PATENT DOCUMENTS

| | | |
|---|---|---|
| WO | 2005/011569 A2 | 2/2005 |
| WO | 2007/136821 A1 | 11/2007 |
| WO | 2007/139742 A1 | 12/2007 |
| WO | 2007/139746 A1 | 12/2007 |
| WO | 2007/139747 A1 | 12/2007 |
| WO | 2007/139748 A1 | 12/2007 |
| WO | 2008/109200 A1 | 9/2008 |
| WO | 2008/109674 A1 | 9/2008 |
| WO | 2008/112845 A1 | 9/2008 |
| WO | 2008/128165 A1 | 10/2008 |

OTHER PUBLICATIONS

International Search Report and Written Opinion, PCT/US2011/027765, Jul. 11, 2011.
International Search Report and Written Opinion, PCT/US2011/055482, Jun. 21, 2012.
Notice of Allowance and Fee(s) Due, U.S. Appl. No. 13/043,933, Dec. 10, 2014.
Notice of Allowance and Fee(s) Due, U.S. Appl. No. 13/043,933, May 28, 2014.
Notice of Allowance and Fee(s) Due, U.S. Appl. No. 12/606,064, Apr. 15, 2015.
Office Action, Japanese Patent Application No. 2001-533424, Nov. 8, 2013 (English language translation included).
Office Action, Japanese Patent Application No. 2001-533424, Sep. 2, 2014 (English language translation included) X.
Office Action, U.S. Appl. No. 12/606,064, Apr. 1, 2014.
Office Action, U.S. Appl. No. 12/606,064, Apr. 6, 2012.
Office Action, U.S. Appl. No. 12/606,064, Nov. 10, 2014.
Office Action, U.S. Appl. No. 12/606,064, Oct. 22, 2013.
Office Action, U.S. Appl. No. 12/606,064, Sep. 4, 2012.
Office Action, U.S. Appl. No. 13/043,933, Aug. 23, 2013.
Office Action, U.S. Appl. No. 13/043,933, Mar., 21, 2013.
Official Communication, European Patent Application No. 09752942.4, Mar. 31, 2015.
Notice of Allowance and Fee(s) Due, U.S. Appl. No. 12/606,064, Oct. 28, 2015.
Official Communication, European Patent Application no. 09752942.4, Feb. 17, 2016.
Gloeckner, Herrna, et al., "New Miniaturized Hollow-Fiber Bioreactor for in Vivo Like Cell Culture, Cell Expansion, and Production of Cell-Derived Products," Biotechnol. Prog., American Chemical Society and American Institute of chemical Engineers, 2001, vol. 17, No. 5, pp. 828-831.
Examination Report No. 1, Australian Patent Application No. 2009320165, Jul. 10, 2014.
Official Communication, European Patent Application No. 09752942.4, Sep. 29, 2016.
Official Communication, European Patent Application No. 11773366.7, Sep. 20, 2016.

* cited by examiner

METHODS AND SYSTEMS OF GROWING AND HARVESTING CELLS IN A HOLLOW FIBER BIOREACTOR SYSTEM WITH CONTROL CONDITIONS

CROSS-REFERENCE TO RELATED APPLICATIONS

This application is a divisional application of, and claims priority to, U.S. patent application Ser. No. 13/269,512, entitled, “Methods and Systems of Growing and Harvesting Cells in a Hollow Fiber Bioreactor System with Control Conditions,”filed on Oct. 7, 2001 and issued as U.S. Pat. No. 8,895,291 on Nov. 25, 2014, which claims the benefit of U.S. Provisional Application Ser. No. 61/391,152, filed on Oct. 8, 2010, and entitled, “Methods of Growing and Harvesting Cells in a Hollow Fiber Bioreactor System” and of U.S. Provisional Application Ser. No. 61/434,726, filed on Jan. 20, 2011, and entitled, “Methods of Growing and Harvesting Cells in a Hollow Fiber Bioreactor System.” The disclosures of the above-identified applications are hereby incorporated by reference in their entireties as if set forth herein in full for all that they teach and for all purposes.

FIELD

Embodiments of the present disclosure relate to cell growth in cell expansion systems.

BACKGROUND

The use of stem cells in a variety of medical treatments and therapies is receiving growing attention. Cell expansion systems can be used to grow stem cells, as well as other types of cells, such as bone marrow cells which may include stem cells. Stem cells which are expanded from donor cells can be used to repair or replace damaged or defective tissues and are considered for treating a wide range of diseases. Cell expansion systems (CESs) are used to expand cells and may be used to expand donor stem cells from bone marrow. Stem cells may be grown in hollow fiber bioreactors in a cell expansion system.

SUMMARY

Embodiments of the present disclosure generally relate to providing a control condition for stopping a process in a cell expansion system. Aspects of particular embodiments further provide for a stop condition involving an air removal chamber used in the cell expansion system. In embodiments, the stop condition is met when air, a lack of fluid, and/or a gas/fluid interface, e.g., an air/fluid interface, is detected in the air removal chamber.

The disclosure relates to a method of controlling a process in a cell expansion system. The method includes the steps of providing a fluid conveyance assembly, wherein the fluid conveyance assembly comprises a bioreactor; engaging the fluid conveyance assembly; providing an air removal chamber, wherein the air removal chamber is mounted on the fluid conveyance assembly, and wherein the air removal chamber comprises a fluid containment chamber, the fluid containment chamber comprising: a fluid entrance aperture, a fluid exit aperture, wherein the fluid exit aperture is coupled to a fluid exit tube, and a vent aperture, wherein the vent aperture is located above the fluid entrance aperture and the fluid exit aperture; providing a pump to pump a fluid through the fluid entrance aperture and into the fluid containment chamber of the air removal chamber; initiating the process, comprising operating the pump to pump the fluid through the fluid entrance aperture and into the fluid containment chamber, wherein the fluid reaches a fluid level in the fluid containment chamber; allowing the fluid to pass through the fluid exit aperture to enter the fluid exit tube; providing a sensor to detect the fluid level in the fluid containment chamber; detecting the fluid level using the sensor; providing a stop condition comprising meeting the stop condition when the fluid level in the fluid containment chamber reaches a predetermined level as detected by the sensor; and when the fluid level in the fluid containment chamber is at the predetermined level, stopping the process based on meeting the stop condition.

In at least one embodiment, providing the stop condition comprises meeting the stop condition when the sensor detects air. In at least one embodiment, providing the sensor comprises providing an ultrasonic sensor. In at least one embodiment, providing the sensor comprises providing an optical sensor. In at least one embodiment, the process comprises chasing the fluid from the air removal chamber. In at least one embodiment, when the fluid level in the fluid containment chamber is higher than the predetermined level, the method includes continuing to pump the fluid through the fluid entrance aperture and into the fluid containment chamber. In at least one embodiment, the process comprises loading media from a media bag into the bioreactor until the media bag is empty, in which the media is the fluid. In at least one embodiment, the process comprises loading cells, in which the media bag is a cell inlet bag. In at least one embodiment, the process comprises loading a reagent, wherein the media bag is a reagent bag. In at least one embodiment, the process comprises a step from a protocol, wherein the protocol comprises one of: loading cells into the bioreactor using a high flux cell load, loading cells into the bioreactor using a load with circulation, adding reagent, releasing adherent cells, or coating the bioreactor. In at least one embodiment, the method includes a second sensor to detect a top level of the fluid level in the fluid containment chamber.

The disclosure also relates to a method of operating a cell expansion system with a stop condition. The method includes the steps of selecting a protocol to load media into a bioreactor of the cell expansion system, wherein the protocol comprises a first process; determining whether a condition for the first process is set; when the condition for the first process is not set, setting the condition; selecting the stop condition for the first process, wherein the stop condition comprises a detection of a gas/fluid interface in an air removal chamber; and selecting to execute the protocol.

In at least one embodiment, the protocol further comprises a second process, in which the first process comprises loading the media from a media bag into the cell expansion system until the media bag is empty, and the second process comprises chasing the media from the air removal chamber into a circulation loop of the cell expansion system. In at least one embodiment, the circulation loop comprises an intracapillary loop. In at least one embodiment, selecting a protocol to load media into the bioreactor comprises selecting the media, the media comprising one of: cells from a cell inlet bag or reagent from a reagent bag. In at least one embodiment, the one or more sensors detect the gas/fluid interface at a predetermined measuring position within the air removal chamber. In at least one embodiment, the one or more sensors comprise an ultrasonic sensor. In at least one embodiment, the protocol comprises one of: loading cells into the bioreactor using a high flux cell load, loading cells into the bioreactor using a load with circulation, adding reagent, releasing adherent cells, or coating the bioreactor.

The disclosure further relates to a cell expansion system comprising a capability to stop a process, in which the stopping of the process is automated. The system includes a fluid conveyance assembly comprising a bioreactor. The system also includes an air removal chamber comprising a fluid containment chamber. The fluid containment chamber comprises a fluid entrance aperture, a fluid exit aperture, and a vent aperture, wherein the vent aperture is located above the fluid entrance aperture and the fluid exit aperture. The system also includes at least one sensor for detecting a fluid in the fluid containment chamber and a controller in communication with the at least one sensor. The controller is operable to: signal to start the process, comprising signaling to start the one or more pumps for pumping the fluid through the fluid entrance aperture and into the fluid containment chamber of the air removal chamber; receive an indication from the at least one sensor when a lack of the fluid is detected by the at least one sensor; and in response to receiving the indication from the at least one sensor, altering the one or more pumps. In at least one embodiment, the altering the one or more pumps comprises stopping the one or more pumps to stop the process.

In at least one embodiment, the process comprises loading, by the one or more pumps, media from a media bag through the air removal chamber and into an intracapillary side of the bioreactor until the media bag is empty, wherein the media is the fluid. In at least one embodiment, the process comprises a step from a protocol, wherein the protocol comprises one of: loading cells into the bioreactor using a high flux cell load, loading cells into the bioreactor using a load with circulation, adding reagent, releasing adherent cells, or coating the bioreactor. In at least one embodiment, the at least one sensor is an ultrasonic sensor, and wherein the at least one sensor detects the lack of fluid by sensing air.

This Summary is included to provide a selection of concepts in a simplified form, in which such concepts are further described below in the Detailed Description. This Summary is not intended to be used in any way to limit the claimed subject matter's scope. Features, including equivalents and variations thereof, may be included in addition to those provided herein.

BRIEF DESCRIPTION OF THE DRAWINGS

Embodiments of the present disclosure may be described by referencing the accompanying figures. In the figures, like numerals refer to like items.

DETAILED DESCRIPTION

The following Detailed Description provides a discussion of illustrative embodiments with reference to the accompanying drawings. The inclusion of specific embodiments herein should not be construed as limiting or restricting the present disclosure. Further, while language specific to features, acts, and/or structures, for example, may be used in describing embodiments herein, the claims are not limited to the features, acts, and/or structures described. A person of skill in the art will understand other embodiments, including improvements, that are within the spirit and scope of the present disclosure.

Embodiments of the present disclosure are generally directed to sterile methods for loading, growing, and harvesting cells in a hollow fiber cell growth chamber of a closed cell expansion system. In further embodiments, sterile methods are provided for loading, growing, and harvesting adherent cells, in particular mesenchymal stem cells, in the hollow fiber cell growth chamber of the closed cell expansion system. A closed system means that the contents of the system are not directly exposed to the atmosphere.

Figure 1:
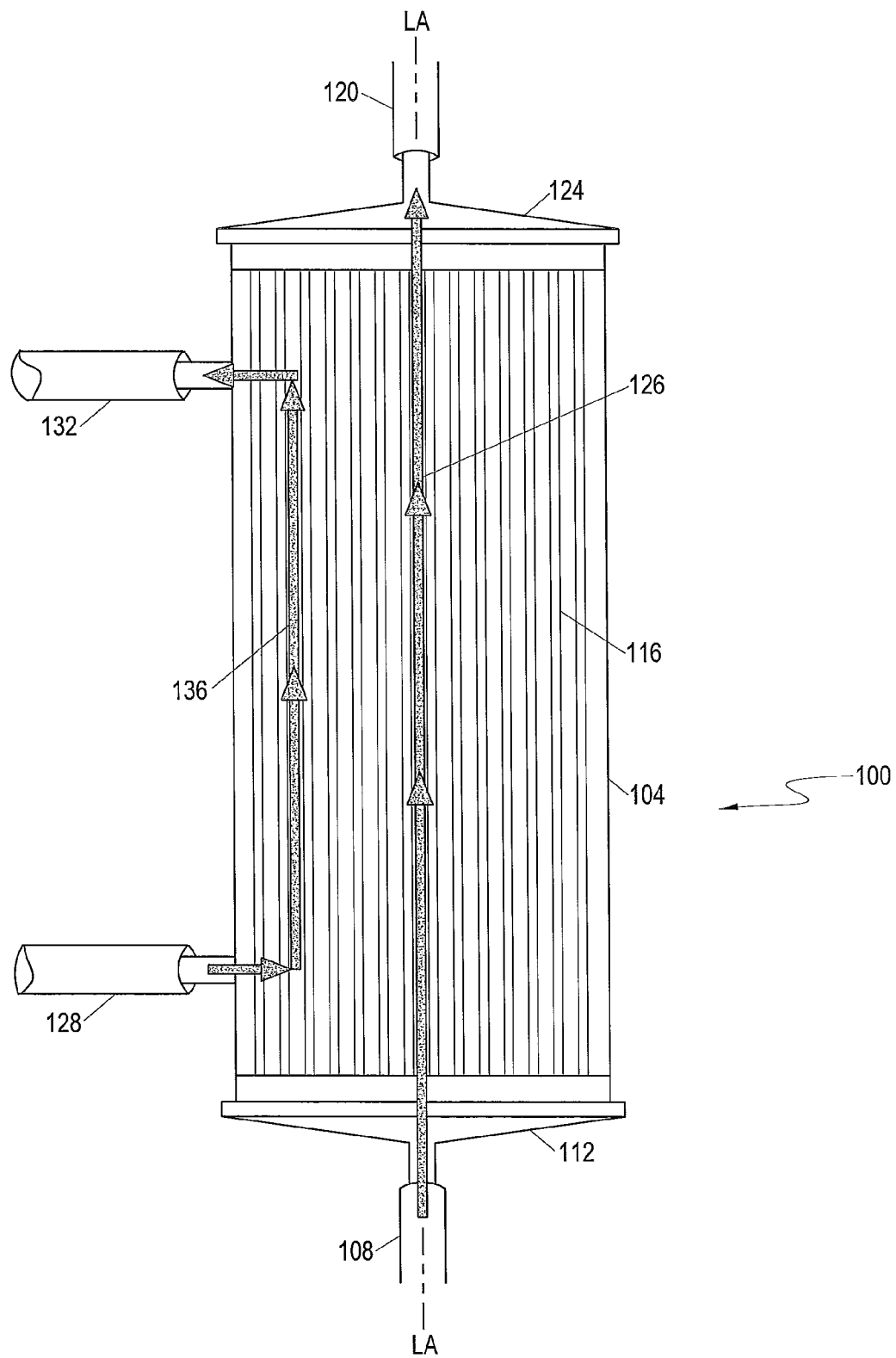
FIG. 1 illustrates a perspective view of a hollow fiber bioreactor in accordance with embodiments of the present disclosure.

With reference now to FIG. 1, an example of a hollow fiber cell growth chamber 100 which may be used with the present disclosure is shown in front side elevation view. Cell growth chamber 100 has a longitudinal axis LA-LA and includes cell growth chamber housing 104. In at least one embodiment, cell growth chamber housing 104 includes four openings or ports: IC inlet port 108, IC outlet port 120, EC inlet port 128, and EC outlet port 132. It should be noted that like elements are represented by like numerals in all of the Figures.

According to embodiments of the present disclosure, fluid in a first circulation path enters cell growth chamber 100 through IC inlet port 108 at a first longitudinal end 112 of the cell growth chamber 100, passes into and through the intracapillary side (referred to in various embodiments as the intracapillary ("IC") side or "IC space" of a hollow fiber membrane) of a plurality of hollow fibers 116, and out of cell growth chamber 100 through IC outlet port 120 located at a second longitudinal end 124 of the cell growth chamber 100. The fluid path between the IC inlet port 108 and the IC outlet port 120 defines the IC portion 126 of the cell growth chamber 100. Fluid in a second circulation path flows in the cell growth chamber 100 through EC inlet port 128, comes in contact with the extracapillary side or outside (referred to as the "EC side" or "EC space" of the membrane) of the hollow fibers 116, and exits cell growth chamber 100 via EC outlet port 132. The fluid path between the EC inlet port 128 and the EC outlet port 132 comprises the EC portion 136 of the cell growth chamber 100. Fluid entering cell growth chamber via the EC inlet port 128 is in contact with the outside of the hollow fibers 116. Small molecules (e.g., ions, water, oxygen, lactate, etc.) can diffuse through the hollow fibers from the interior or IC space of the hollow fiber to the exterior or EC space, or from the EC space to the IC space. Large molecular weight molecules such as growth factors are typically too large to pass through the hollow fiber membrane, and remain in the IC space of the hollow fibers. The media may be replaced as needed. Media may also be circulated through an oxygenator 232 (FIG. 2) to exchange gasses as needed. Cells can be contained within the first circulation path 202 and/or second circulation path 204 as described below, and can be on either the IC side and/or EC side of the membrane.

The material used to make the hollow fiber membrane may be any biocompatible polymeric material which is capable of being made into hollow fibers. One material which may be used is a synthetic polysulfone-based material, according to an embodiment of the present disclosure. In order for the cells to adhere to the surface of the hollow fibers, the surface may be modified in some way, either by coating at least the cell growth surface with a protein such as fibronectin or collagen, or by exposing the surface to radiation. A gamma irradiated polysulfone-based membrane for cell expansion is described in WO 2010/034466. Gamma treating the membrane surface allows for attachment of adherent cells without additionally coating the membrane with fibronectin or the like. Bioreactors made of gamma treated membranes can be reused.

Figure 2:
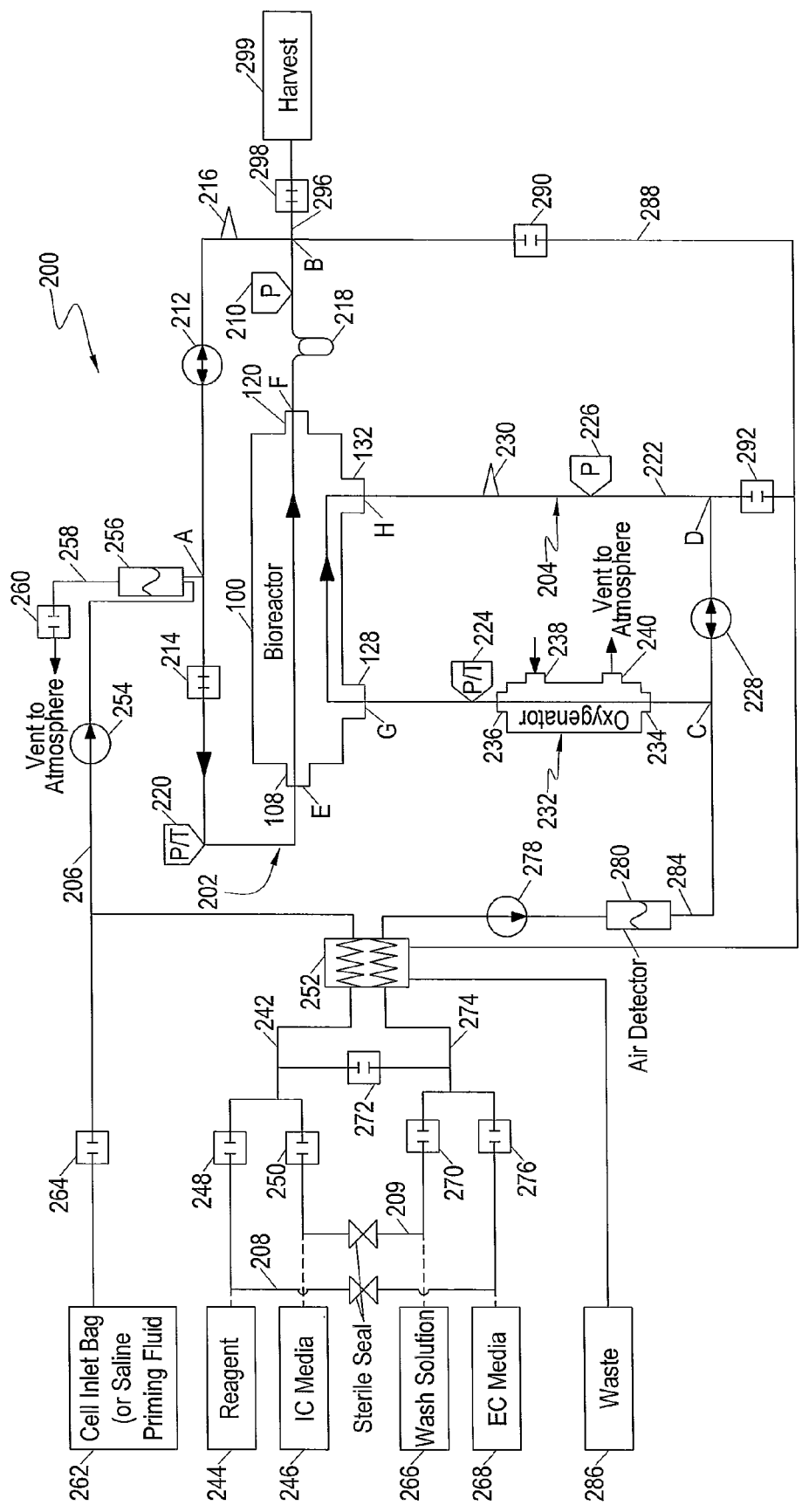
FIG. 2 depicts a schematic of one embodiment of a cell expansion system.

Referring now to FIG. 2, a schematic of one possible embodiment of a cell expansion system (CES) which may be used with the present disclosure is shown. In this embodiment and in all the examples or protocols below, the cells are grown in the IC space. CES 200 includes first fluid circulation path 202 (also referred to as the "intracapillary loop" or "IC loop") and second fluid circulation path 204 (also referred to as the "extracapillary loop" or "EC loop"). First fluid flow path 206 is fluidly associated with cell growth chamber 100 to form first fluid circulation path 202. Fluid flows into cell growth chamber 100 through IC inlet port 108, through hollow fibers in cell growth chamber 100, and exits via IC outlet port 120. Pressure gauge 210 measures the pressure of media leaving cell growth chamber 100. Media flows through IC circulation pump 212 which can be used to control the rate of media flow. IC circulation pump 212 may pump the fluid in a first direction or second direction opposite the first direction. Exit port 120 can be used as an inlet in the reverse direction. Media entering the IC loop may enter through valve 214. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the CES and modifications to the schematic shown are within the scope of the one or more present embodiments.

With regard to the IC loop, samples of media can be obtained from sample port 216 or sample coil 218 during operation. Pressure/temperature gauge 220 disposed in first fluid circulation path 202 allows detection of media pressure and temperature during operation. Media then returns to IC inlet port 108 to complete fluid circulation path 202. Cells grown/expanded in cell growth chamber 100 can be flushed out of cell growth chamber 100 into harvest bag 299 through valve 298 or redistributed within the hollow fibers for further growth. This will be described in more detail below. In this example, cells are grown in the IC space.

Fluid in second fluid circulation path 204 enters cell growth chamber 100 via EC inlet port 128, and leaves cell growth chamber 100 via EC outlet port 132. Media in the EC loop is in contact with the outside of the hollow fibers in the cell growth chamber 100, thereby allowing diffusion of small molecules into and out of the hollow fibers.

Pressure/temperature gauge 224 disposed in the second fluid circulation path 204 allows the pressure and temperature of media to be measured before the media enters the EC space of the cell growth chamber 100. Pressure gauge 226 allows the pressure of media in the second fluid circulation path 204 to be measured after it leaves the cell growth chamber 100. With regard to the EC loop, samples of media can be obtained from sample port 230 or a sample coil (not shown) during operation.

After leaving EC outlet port 132 of cell growth chamber 100, fluid in second fluid circulation path 204 passes through EC circulation pump 228 to oxygenator 232. EC circulation pump 228 may also pump the fluid in opposing directions. Second fluid flow path 222 is fluidly associated with oxygenator 232 via oxygenator inlet port 234 and oxygenator outlet port 236. In operation, fluid media flows into oxygenator 232 via oxygenator inlet port 234, and exits oxygenator 232 via oxygenator outlet port 236. Oxygenator 232 adds oxygen to and removes bubbles from media in the CES. In various embodiments, media in second fluid circulation path 204 is in equilibrium with gas entering oxygenator 232. The oxygenator 232 can be any appropriately sized oxygenator or gas transfer device known in the art. Air or gas flows into oxygenator 232 via filter 238 and out of oxygenator or gas transfer device 232 through filter 240. Filters 238 and 240 reduce or prevent contamination of oxygenator 232 and associated media. Air or gas purged from the CES 200 during portions of a priming sequence can vent to the atmosphere via the oxygenator 232.

In the configuration depicted for CES 200, fluid media in first fluid circulation path 202 and second fluid circulation path 204 flows through cell growth chamber 100 in the same direction (a co-current configuration). The CES 200 can also be configured to flow in a counter-current conformation.

In accordance with at least one embodiment, media, such as cells (from bag 262), and fluid media from bag 246 can be introduced to first fluid circulation path 202 via first fluid flow path 206. Fluid containers, or media bags, 244 (e.g., Reagent) and 246 (e.g., IC Media) may be fluidly associated with either first fluid inlet path 242 via valves 248 and 250, respectively or second fluid inlet path 274 via valves 270 and 276. First and second sterile sealable input priming paths 208 and 209 are provided. Air removal chamber (ARC) 256 is fluidly associated with first circulation path 202. The air removal chamber 256 may include one or more ultrasonic sensors including an upper sensor 1268 and lower sensor 1264 to detect air, a lack of fluid, fluid, and/or a gas/fluid interface, e.g., an air/fluid interface, at certain measuring positions within the air removal chamber 256 (see FIG. 6), and to send a signal to the controller upon such detection, according to embodiments of the present disclosure. For example, ultrasonic sensors may be used near the bottom and/or near the top of the air removal chamber 256 to detect air, a lack of fluid, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 200 during portions of the priming sequence or other protocols can vent to the atmosphere out air valve 260 via line 258 that is fluidly associated with air removal chamber 256.

Fluid container 262 (e.g., Cell Inlet Bag (or Saline Priming Fluid for priming air out of the system)) is fluidly associated with the first fluid circulation path 202 via valve 264.

EC media (from bag 268) or wash solution (from bag 266) may be added to either the first or second fluid flow path. Fluid container 266 may be fluidly associated with valve 270 that is fluidly associated with first fluid circulation path 202 via distribution valve 272 and first fluid inlet path 242. Alternatively, fluid container 266 can be fluidly associated with second fluid circulation path 204 via second fluid inlet path 274 and second fluid flow path 284 by opening valve 270 and closing distribution valve 272. Likewise, fluid container 268 is fluidly associated with valve 276 that may be fluidly associated with first fluid circulation path 202 via first fluid inlet path 242 and distribution valve 272. Alternatively, fluid container 268 may be fluidly associated with second fluid inlet path 274 by opening valve 276 and closing valve distribution 272.

An optional heat exchanger 252 may be provided for media reagent or wash solution introduction.

In the IC loop, fluid is initially advanced by the IC inlet pump 254. In the EC loop, fluid is initially advanced by the EC inlet pump 278. An air detector 280, such as an ultrasonic sensor, may also be associated with the EC inlet path 284.

In at least one embodiment, first and second fluid circulation paths 202 and 204 are connected to waste line 288. When valve 290 is opened, IC media can flow through waste line 288 and to waste bag 286. Likewise, when valve 292 is opened, EC media can flow through waste line 288 to waste bag 286.

Cells can be harvested via cell harvest path 296. Here, cells from cell growth chamber 100 can be harvested by pumping the IC media containing the cells through cell harvest path 296 and valve 298 to cell harvest bag 299.

Various components of the CES 200 can be contained or housed within an incubator machine or housing 304 (FIG. 3), wherein the incubator maintains cells and media at a desirable temperature.

Figure 3:
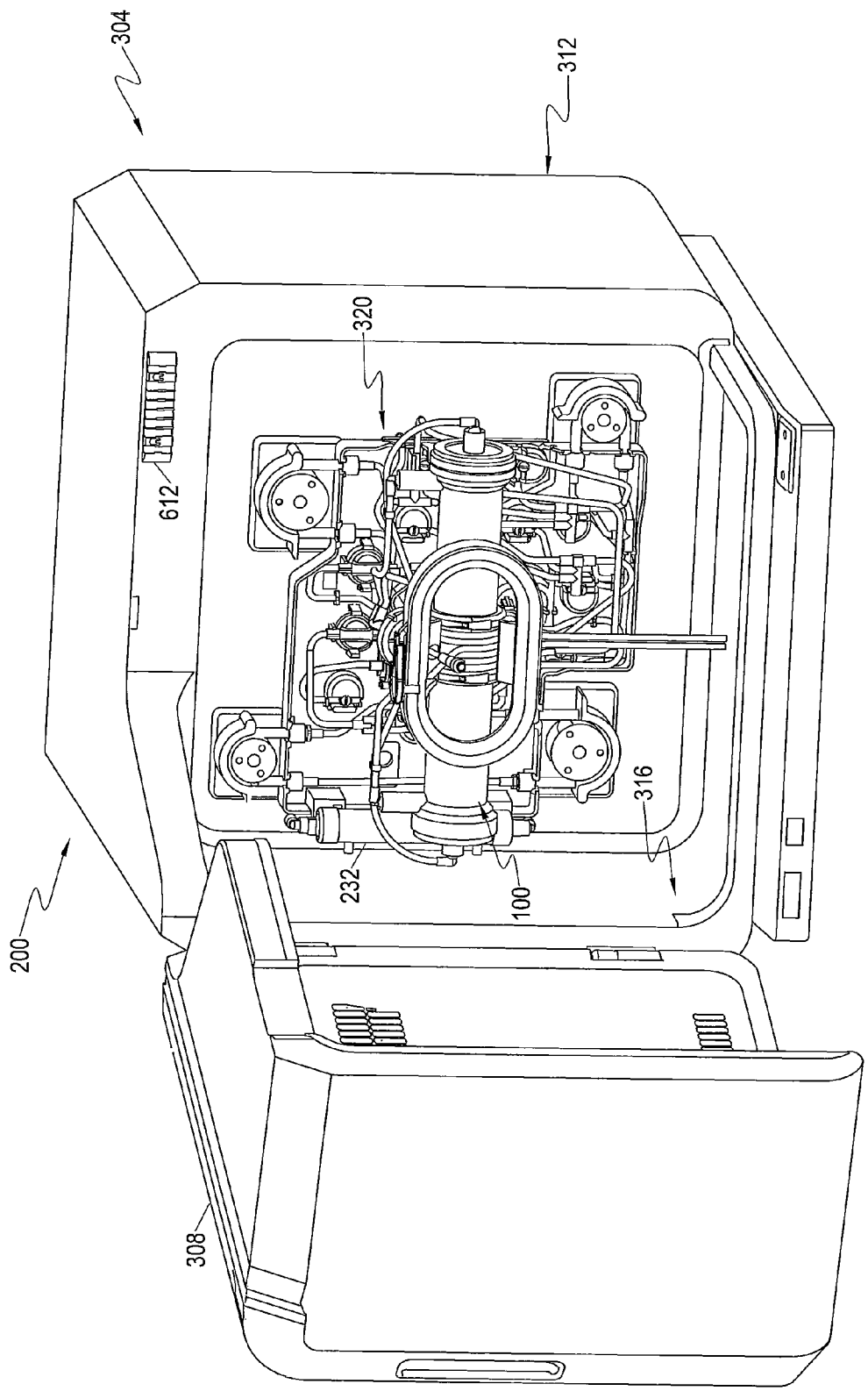
FIG. 3 illustrates a perspective view of the cell expansion system with a pre-mounted fluid conveyance device in accordance with embodiments of the present disclosure.

With reference now to FIG. 3, an embodiment of a CES 200 is shown. The CES 200 includes a cell expansion housing or machine 304 that comprises a hatch or closable door 308 for engagement with a back portion 312 of the cell expansion machine 200. An interior space 316 within the cell expansion machine 304 includes features adapted for receiving and engaging a premounted fluid conveyance assembly 320. The premounted fluid conveyance assembly 320 is detachably-attachable to the cell expansion machine 200 to facilitate relatively quick exchange of a new or unused premounted fluid conveyance assembly 320 at a cell expansion machine 200 for a used premounted fluid conveyance assembly 320 at the same cell expansion machine 200. Advantageously, a single cell expansion machine 304 can be operated to grow or expand a first set of cells using a first premounted fluid conveyance assembly 320, and thereafter, used to grow or expand a second set of cells using a second premounted fluid conveyance assembly 320 without needing to be sanitized between interchanging the first premounted fluid conveyance assembly 320 for the second premounted fluid conveyance assembly 320. The premounted fluid conveyance assembly includes the bioreactor 100 and the oxygenator 232. Tubing guide slots are shown as 612 for receiving various media tubing connected to premounted fluid conveyance assembly 320.

Figure 4:
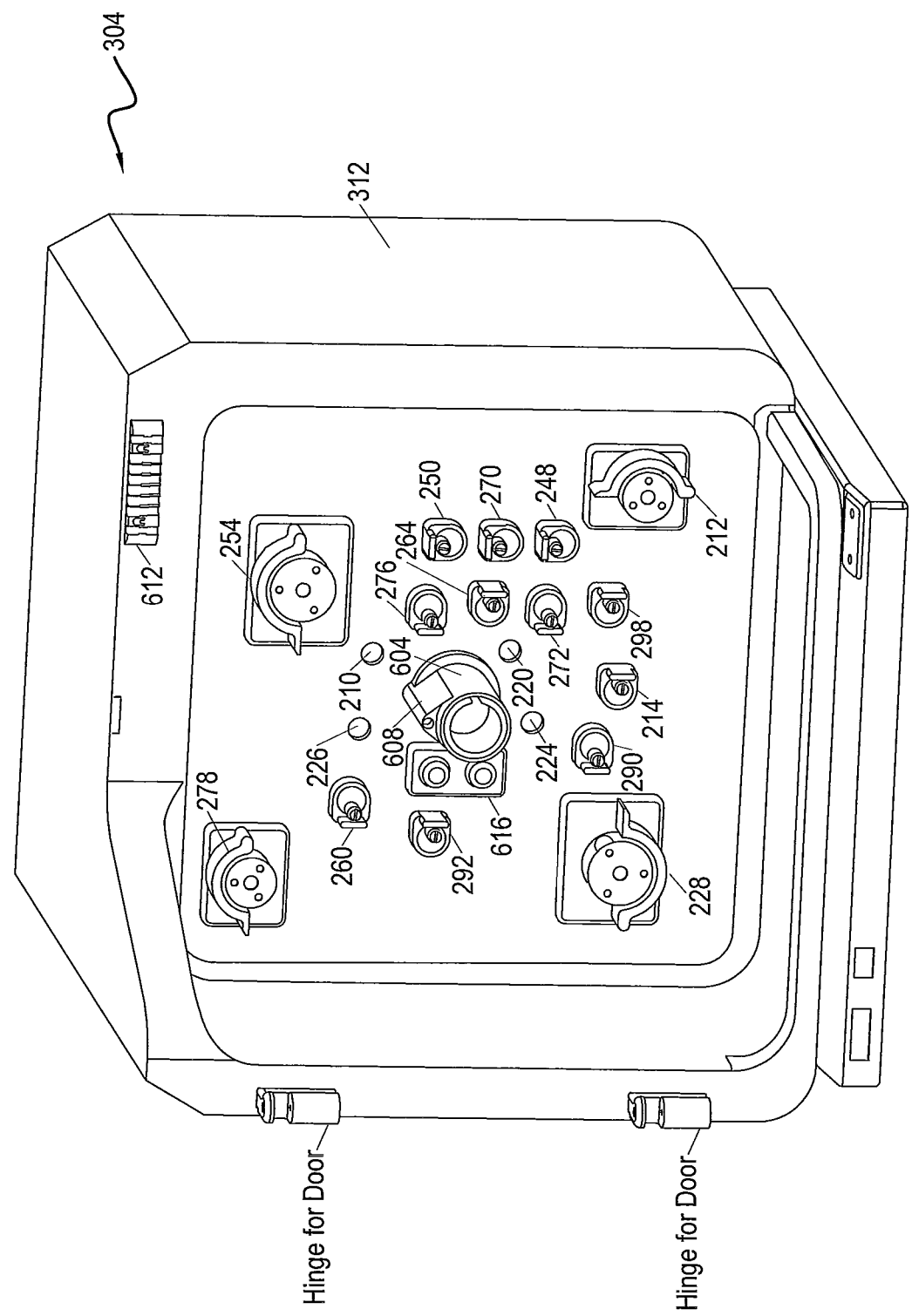
FIG. 4 depicts a perspective view of the housing of the cell expansion system in accordance with embodiments of the present disclosure.

Referring now to FIG. 4, the back portion 312 of a cell expansion machine 304 is shown prior to detachably-attaching a premounted fluid conveyance assembly 320. For clarity, the closable door 308 (shown in FIG. 3) is omitted from FIG. 4. The back portion 312 of the cell expansion machine 304 includes a number of different structures for working in combination with elements of a premounted fluid conveyance assembly 320. More particularly, the back portion 312 of the cell expansion machine 304 includes a plurality of peristaltic pumps for cooperating with pump loops 404 (FIG. 5), including the IC circulation pump 212, the EC circulation pump 228, the IC inlet pump 254, and the EC inlet pump 278. In addition, the back portion 312 of the cell expansion machine 104 includes a plurality of valves, including the IC circulation valve 214, the reagent valve 248, the IC media valve 250, the air removal valve 260, the cell inlet valve 264, the wash valve 270, the distribution valve 272, the EC media valve 276, the IC waste valve 290, the EC waste valve 292, and the harvest valve 298. Several sensors are also associated with the back portion 312 of the cell expansion machine 304, including the IC outlet pressure sensor 210, the combination IC inlet pressure and temperature sensors 220, the combination EC inlet pressure and temperature sensors 224, and the EC outlet pressure sensor 226. Also shown is the optical sensor 616 for the air removal chamber 256.

Referring still to FIG. 4, a shaft or rocker control 604 for rotating the bioreactor 100 is shown. Shaped fitting 608 associated with the shaft 604 allows for proper alignment of a shaft access aperture 324 (FIG. 5) of the tubing-organizer 300 of the premounted conveyance assembly with the back portion 312 of the cell expansion machine 304. Rotation of rocker control 604 imparts rotational movement to shaft fitting 508 (FIG. 5) and bioreactor 100. Thus, when an operator of the CES 200 attaches a new or unused premounted fluid conveyance assembly 320 to the cell expansion machine 304, the alignment is a relatively simple matter of properly orienting the shaft access aperture 324 of the premounted fluid conveyance assembly 320 with the shaped fitting 608.

Figure 5:
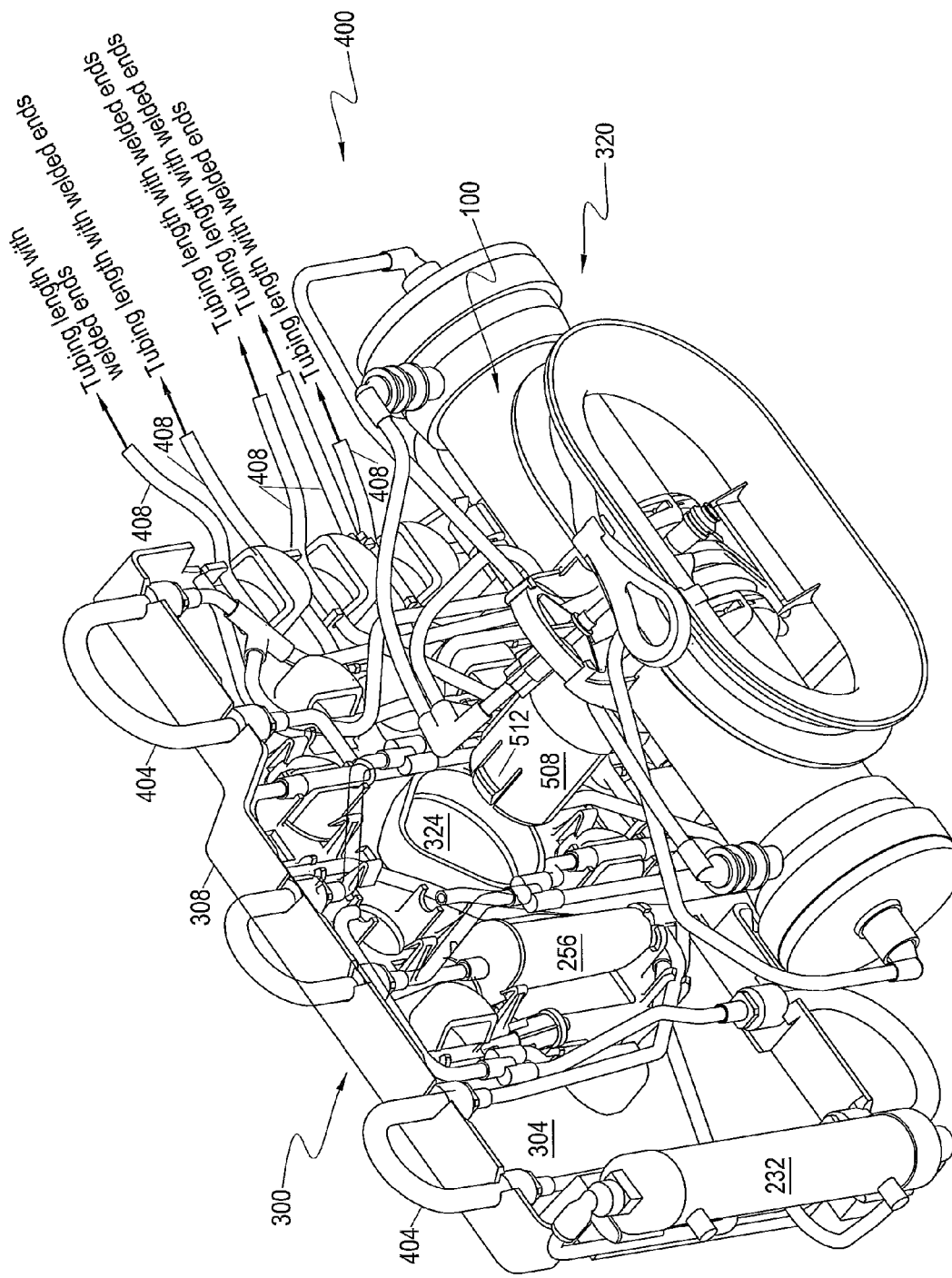
FIG. 5 illustrates a perspective view of the pre-mounted fluid conveyance device in accordance with embodiments of the present disclosure.

Referring now to FIG. 5, a perspective view of a detachably-attachable premounted fluid conveyance assembly 320 is shown. The premounted fluid conveyance assembly 320 is detachably-attachable to the cell expansion housing 304 to facilitate relatively quick exchange of a new or unused premounted fluid conveyance assembly 320 at a cell expansion machine 304 for a used premounted fluid conveyance assembly 320 at the same cell expansion machine 304. As shown in FIG. 5, the bioreactor 100 is attached to a bioreactor coupling that includes a shaft fitting 508. The shaped fitting 508 includes one or more shaft fastening mechanisms, such as a biased arm or spring member 512 for engaging a shaft (shown in FIG. 4) of the cell expansion machine 304.

Referring still to FIG. 5, the premounted fluid conveyance assembly 320 typically includes tubing 408 and various tubing fittings 412 to provide the fluid paths shown in FIG. 2. Pump loops 404 are also provided for the pump. Although the various media are typically provided at the site where the cell expansion machine 304 is located, the premounted fluid conveyance assembly 320 typically includes sufficient tubing length to extend to the exterior of the cell expansion machine 304 and to enable welded connections to tubing associated with the media bags.

Figure 6:
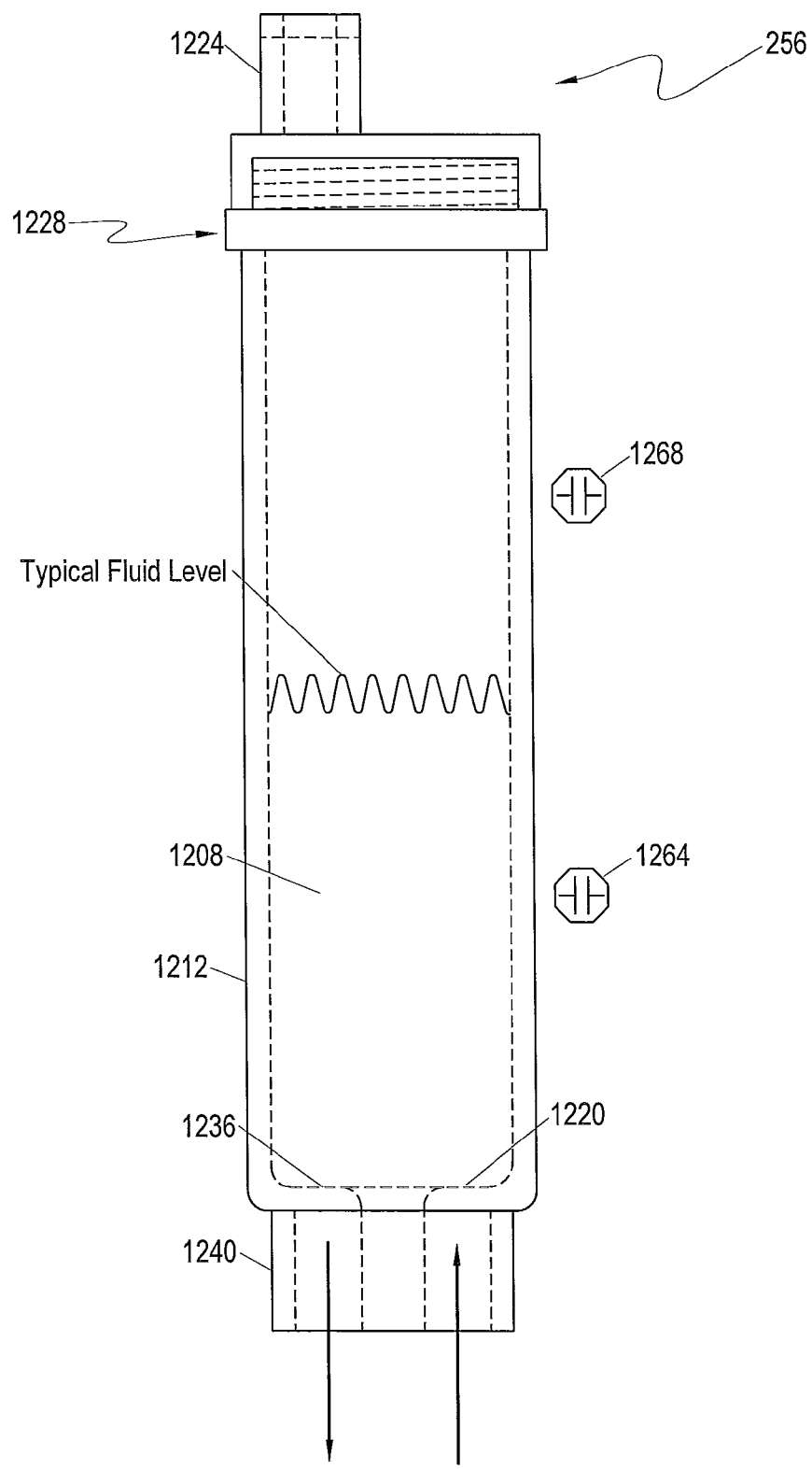
FIG. 6 depicts a perspective view of the air removal chamber in accordance with embodiments of the present disclosure.

The air removal chamber or ARC will now be described with respect with FIG. 6. In accordance with at least one embodiment, the air removal chamber 256 is mounted in a substantially vertical orientation on the premounted fluid conveyance assembly 320, such that air or gas bubbles within the fluid rise upward away from the bottom 1212 toward the vent aperture 1224 preferably located at the top 1228 along the vertical direction of the air removal chamber 256, or at least vertically above the fluid entrance aperture 1220 and fluid exit aperture 1236.

Referring again to FIG. 6 in at least one embodiment a plurality of fluid level sensors is used in combination with the air removal chamber 256. In at least one embodiment, the sensors are located on the cell expansion machine 304 at 616. More particularly, while the air removal chamber 256 is connected to a premounted fluid conveyance assembly 320 that can be detachably-attached to the cell expansion machine 304, the fluid level sensors for the air removal chamber 256 form part of the cell expansion machine 304 along with a control for such.

In accordance with at least one embodiment, at least two sensors are used with the air removal chamber 256 to provide "high" and "low" fluid level sensing capability. Accordingly, operating protocol for the CES 100 includes monitoring the fluid level within the air removal chamber 256 and adjusting the pumping rate of the peristaltic pumps as necessary to maintain an appropriate fluid level within the fluid containment chamber 1208 of the air removal chamber. This operating protocol may include increasing or decreasing the pumping rates associated with pumps on either one or both the upstream and downstream sides of the air removal chamber 256. The ARC as described below also functions as a stop indication for various protocols. In embodiments using the ARC as a stop indication, the stopping of a process is automated based on the detection of air, a lack of fluid, and/or a gas/fluid interface in the air removal chamber.

In at least one embodiment, a first fluid level sensor 1264 (or low level fluid sensor) is situated to detect a fluid level in the air removal chamber 256 at a level of approximately ¼ full, and a second fluid level sensor 1268 (or high level fluid sensor) is situated to detect a fluid level in the air removal chamber 256 at a level of approximately ¾ full. The position of the fluid level sensors 1264 and 1268 allow the fluid level within the air removal chamber 256 to be adjusted to ensure that air does not pass though the fluid exit aperture 1236 and enter the fluid exit tube 1240 at the bottom 1212 of the air removal chamber 256 because of too low a fluid level, and that fluid does not exit through vent aperture 1224 located at the top 1228 of the air removal chamber 256 because of too high a fluid level.

As will be recognized by those of skill in the art, any number of fluid containers (e.g., media bags) can be fluidly associated with the CES in any combination.

Protocols will now be described with respect to the schematic described in FIG. 2, in accordance with embodiments of the present disclosure.

The following is a definition section for the Protocols described below. Points A through H on the schematic of FIG. 2 are also described in the definition section below. In the protocols or examples described the definition section may be referenced for various descriptions.

Protocols Parameter Definitions

| Parameter | Value | Explanations |
|---|---|---|
| VOLUME (mL) | | |
| $V_{ICL}$ | 189.1 | IC Loop Volume, $V_{BRIC} + 2V_{BRICH} + V_{EF}$ |
| $V_{ECL}$ | 305.6 | EC Loop Volume, $V_{BREC} + V_{GH}$ |
| $V_{ICBL}$ | 29.3 | Volume from bags to IC Loop, ARC volume is assumed to be 10 mL, inlet bag length assumed to be 3 mL |
| $V_{ECBL}$ | 18.5 | Volume from bags to EC Loop, inlet bag length assumed to be 3 mL |
| $V_{ICE}$ | 218.4 | IC Exchange volume = $V_{ICL} + V_{ICBL}$ |
| $V_{ECE}$ | 324.1 | EC Exchange volume = $V_{ECL} + V_{ECBL}$ |
| $V_{ABI}$ | 9 | Point "A" on FIG. 2 to Bioreactor inlet (includes header volume), excludes value directly from ARC to T-junction |
| $V_{ABO}$ | 42.1 | Point "A" of FIG. 2 to Bioreactor outlet (includes header volume), excludes value directly from ARC to T-junction |
| $V_{AB}$ | 32.6 | Volume from point "A" to point "B" of FIG. 2 |
| $V_{CD}$ | 3.8 | Volume from point "C" to point "D" of FIG. 2 |
| $V_{ARC}$ | 11.1 | Volume used to flush ARC contents into IC Loop = $V_{ARCA} + V_{ARCBS}$ |
| $V_{BRIC}$ | 138 | Volume of the IC side of bioreactor, excludes headers |
| $V_{BRICH}$ | 4.5 | Volume of IC header |
| $V_{EF}$ | 42.1 | Volume from Point "E" to Point "F" IC loop of FIG. 2 excluding bioreactor |
| $V_{BREC}$ | 266 | Volume of the EC side of the bioreactor |
| $V_{GH}$ | 39.6 | Volume from Point "G" to Point "H" EC loop of FIG. 2 excluding bioreactor |
| $V_{FA}$ | 37.6 | Volume from Point "F" to Point "A" IC loop of FIG. 2 excluding bioreactor |
| $V_{EA}$ | 4.5 | Volume from Point "E" to Point "A" IC loop of FIG. 2 excluding bioreactor |
| $V_{ARCA}$ | 4.1 | Volume from the bottom sensor of the ARC to Point "A" of FIG. 2 |
| $V_{ARCBS}$ | 7 | Volume of ARC between sensors |
| $V_{ARCF}$ | 2 | Volume to fill above ARC top sensor |
| $V_{FTO}$ | 40.2 | (1 + LP %/100) * $V_{ICBL}$ + 5 mL |
| $V_{PICBR}$ | 157.4 | Line volume being primed for IC side of bioreactor |
| $V_{PICCP}$ | 33 | Line volume being primed for IC Circulation pump |
| $V_{PECCP}$ | 4.6 | Line volume being primed for EC Circulation pump |
| $V_{PREL}$ | 20.9 | Line volume being primed for Reagent/EC Media loop |
| $V_{PWIL}$ | 20 | Line volume being primed for Wash/IC Media loop |
| $V_{PECBR}$ | 308.3 | Line volume being primed for Dist. Valve and EC bioreactor |
| $V_{ICPARC}$ | 6.5 | Volume from the bottom of the ARC to the IC inlet pressure pod includes pressure pod. |
| $V_{MTBS}$ | 18.6 | Maximum volume to bottom ARC sensor |
| $V_{MTTS}$ | 25.6 | Maximum volume to top ARC sensor ($V_{MTBS} + V_{ARCBS}$) |
| $V_{MTECS}$ | 33.1 | Maximum volume to EC fluid sensor |
| $V_{ABO}$ % | 82.4% | = $V_{ABO}$ * 100/($V_{ABI} + V_{ABO}$) |
| AB % | 17.2% | = $V_{AB}$ * 100/$V_{ICL}$ |
| CD % | 1.2% | = $V_{CD}$ * 100/$V_{ECE}$ |
| SP % | 20% | Pump error to be added to a volume from a small pump |
| LP % | 20% | Pump error to be added to a volume from a large pump |
| POINTS ON HYDRAULIC LAYOUT AS SHOWN ON FIG. 2 | | |
| A | | T-junction immediately below the ARC where IC fluid enters the IC loop. |
| B | | Location in the IC Loop where fluid leaves the loop on its way to the Waste Bag |

-continued

| Parameter | Value | Explanations |
|---|---|---|
| C | | T-junction where EC fluid enters the EC loop. |
| D | | Location in the EC Loop where fluid leaves the loop on its way to the Waste Bag. |
| E | | Location in the IC Loop where the line meets the IC Inlet header. |
| F | | Location in the IC Loop where the line meets the IC Outlet header. |
| G | | Location in the EC Loop where the line meets the EC Inlet of the bioreactor. |
| H | | Location in the EC Loop where the line meets the EC Outlet of the bioreactor. |
| PUMP RATES (mL/min) | | |
| $Q_{ICA}$ | | IC Inlet Pump rate (mL/min) |
| $Q_{ICC}$ | | IC Circulation Pump rate (mL/min) |
| $Q_{ECA}$ | | EC Inlet Pump rate (mL/min) |
| $Q_{ECC}$ | | EC Circulation Pump rate (mL/min) |
| $Q_{ECCM}$ | 30 | EC Circulation Pump rate to keep EC Loop well mixed |
| $Q_{ECCE}$ | 250 | EC circulation pump rate to equilibrate EC loop |
| $Q_{ICCM}$ | 20 | IC Circulation Pump rate to keep IC Loop well mixed while preventing air from entering the bioreactor fibers ($Q_{ICC} + Q_{ICA} = Q_{ICCM}$) |
| $Q_{ICCE}$ | 100 | IC circulation pump rate to equilibrate IC loop |
| $Q_{ECAUF}$ | 50 | EC Inlet rate to create ultra filtration |
| $Q_{ARC}$ | 200 | Max flow rate that does not cause air entrapment when ARC fluid level is at low level sensor when running |
| $Q_{FARC}$ | 40 | IC Inlet pump rate (mL/min) used to fill ARC. |
| $UFR_{400}$ | 60 | Negative UFR required to insure zero TMP at the bioreactor outlet when in co-current flow and when IC Inlet rate = 400 mL/min and EC waste valve is closed. |
| TIME (min) | | |
| $T_{CM}$ | 10 | Time to equilibrate (condition) media |

Note:
For all examples the initial position of the bioreactor 100 to define rocker control motion is as shown in FIG. 3 or parallel to the horizon.

Protocol 1: High Flux Cell Load in Bioreactor Example

In an embodiment, this protocol is to load the cells from cell inlet bag 262 into bioreactor 100 until the bag 262 is empty. This is a high flux load at a medium flow rate.

$V_{ICBL}$ is the volume from the bags such as cell inlet bag 262 to the IC loop 202. In this example, the $V_{ICBL}$ is 29.3 mL assuming the volume of the air removal chamber (ARC) is 10 mL and the inlet bag 262 length, such as cell inlet bag 262, is 3 mL.

For a high flux cell load, $V_{FTO}$ of air is needed in the cell inlet bag. $V_{FTO}$ is defined as $(1+LP\%/100)*V_{ICBL}+5$ mL. In this example, it is 40.2 mL. LP % is a percentage related to pump error volume and in this example may be 20%.

The High Flux Load Protocol conditions are:

1) Valve 264 is open.
2) Inlet Pump 254 pumps at 50 mL/min (can be within 20 to 100 mL/min range).
3) IC circulation pump 212 and EC inlet pump 278 are off.
4) EC circulation pump 228 is set at $Q_{ECCM}$ which is a rate selected to keep EC loop well mixed which in this example is 30 mL/min.
5) IC Valve 290 is open to waste.
6) The bioreactor 100 is rotated using the rocker control from −90° to 180° with 1 second rest at end points to distribute cells. Alternatively the bioreactor can be fixed.
7) The high flux cell load is stopped when air is detected in the air removal chamber or ARC by the lower air sensor 1264.
8) ARC valve 260 is open to vent ARC air to atmosphere.
9) The ARC is then filled with media (either reagent, IC media or wash solution) by pump 254 to upper sensor 1268). IC media may be at least 60 mL of media with protein.
10) Cells are chased from the ARC by the fill media of item 9) above to the bioreactor 100 with larger chase volumes spreading the cells toward the IC outlet 120.

11) The chase is stopped at a selected IC volume which in this example is 47 mL.

The following is a brief summary of Protocol High Flux Load with chase step.

Protocol 1 High Flux Load

Purpose of protocol: Loads cells into the bioreactor from the cell inlet bag until the bag is empty. This protocol does not use IC circulation to distribute the cells.

Step 1: Load Bioreactor

Purpose of Step: Loads the cells from the cell inlet bag into the bioreactor.

Precondition: Need at least $V_{FTO}$ of air in cell inlet bag.

| | Input Range |
|---|---|
| IC Source | Cell Inlet |
| EC Source | None |
| Stop Condition | ARC Stop |
| IC Inlet Rate (mL/min) | Default: 50 |
| | Range: 20 to 100 mL/min |
| IC Circulation Rate (mL/min) | Default: 0 |
| EC Inlet Rate (mL/min) | Default: 0 |
| EC Circulation Rate (mL/min) | Default: $Q_{ECCM}$ |
| | Range: 10 to 300 mL/min |
| Outlet | EC Waste |
| Rocker Control | On or in motion          Range: full range |
| | (−90°, 180, 1 sec) (Def) |
| | Fixed (0°)          Range: full range (deg) |
| Output: IC volume | rate as defined by Stop Condition |
| Output: EC volume | N/A |
| Output: Remaining time of step | ARC Stop as defined by Stop Condition |

Step 2: Chase to Bioreactor

Purpose of Step: Chases the cells from the ARC to the bioreactor. Larger chase volumes spread the cells and move them towards the IC outlet.

Precondition: Fill ARC

| | Input Range |
|---|---|
| IC Source | Reagent |
| | IC Media (Default) |
| | Wash |
| | EC Media |
| EC Source | None |
| Stop Condition | IC volume: $(V_{ARCA} + V_{ARCBS} + V_{EA}) * 3$ |
| | Range: 1 to 200 mL |
| IC Inlet Rate (mL/min) | Default: Same as Step 1 |
| IC Circulation Rate (mL/min) | Default: Same as Step 1 |
| EC Inlet Rate (mL/min) | Default: 0 |
| EC Circulation Rate (mL/min) | Default: Same as Step 1 |
| Outlet | EC Waste |
| Rocker Control | Same as Step 1 |
| Output: IC volume | Volume as defined by Stop Condition |
| Output: EC volume | N/A |
| Output: Remaining time of step | Countdown in minutes as defined by Stop Condition |

Protocol 2: Load Cells into Bioreactor with Circulation Example

In an embodiment, this alternative protocol loads the cells from the IC inlet bag 262 until it is empty to the bioreactor 100. It uses the IC circulation loop 202 for the load. The cell inlet bag contains at least $V_{FTO}$ of air. The IC circulation pump 212 permits load from both the inlet 108 and outlet 120 of bioreactor 100.

The conditions for the Protocol Load Cells into Bioreactor with Circulation are:

1) Valve 264 is open.

2) Inlet pump 254 operates at 50 mL/min within a range of 200 to 100 mL/min.

3) IC circulation rate using pump 212 is $V_{ICL}/\text{min} - Q_{ICA}$ $V_{ICL}$, is the IC loop 202 volume or $V_{BRIC} + 2 V_{BRICH} + V_{EF}$ $V_{BRIC}$ is the volume of the IC side of bioreactor 100 excluding headers. $V_{BRICH}$ is the volume of the headers. $V_{EF}$ is the volume of the IC loop from E to F on FIG. 2 excluding the bioreactor.

$Q_{ICA}$ is the inlet pump rate. The range for the IC circulation rate is from 20 to 300 mL/min and depends on the IC inlet rate. In this example it is 139 mL/min.

4) EC inlet is 0 with default $Q_{ECCM}$ in a range from 10 to 300 mL/min.

5) The EC circulation rate is $Q_{ECCM}$, for example 30 mL/min.

6) The outlet the EC waste through valve 292.

7) Rocker control for the bioreactor 100 is −90° to 180° for 1 second stops at the ends of rotation or optionally the bioreactor may be fixed.

8) The stop condition is air detection by the ARC by the lower air sensor 1264.

9) After stop condition ARC is filled with desired media to upper sensor 1268 and chase liquid chases the cells from the ARC to the loop. The stop condition for chase is the IC volume $(V_{ARCA} + V_{ARCBS})*2$ in a range from 1 to 100. $V_{ARCA}$ is the volume from the ARC to point A on FIG. 2 and $V_{ARCBS}$ is the volume of the ARC between sensors 1268 and 1264.

10) To load the cells from the IC loop the IC circulation rate is $-V_{ABO}$ % of $Q_{ICA}$. $-V_{ABO}$% is $V_{ABO}*100/V_{ABI} + V_{ABO}$. $V_{ABO}$ is the volume from point A to the bioreactor 100 outlet (point F) and in this example is 42.1 mL. $Q_{ICA}$ is the inlet pump rate as described above. $V_{ABI}$ is the volume from point A to inlet 108 with $V_{ABO}$ being the volume from point A to outlet 120.

11) The stop condition for the load is the IC volume $1.5 \times V_{EF}$. The range is $0.5 V_{EF}$ to $2.0 V_{EF}$. $V_{EF}$ is the volume of the IC loop 202 from point E to F excluding the bioreactor.

Below is a summary of the circulation load.

Protocol 2 Load with Circulation

Purpose of protocol: Loads the cells into the bioreactor from the cell inlet bag until the bag is empty, and uses IC circulation to distribute the cells.

Step 1: Load IC Loop

Purpose of Step: Loads the cells into the system.

Precondition: Need at least $V_{FTO}$ of air in cell inlet bag.

| | Input Range | |
|---|---|---|
| IC Source | Cell Inlet | |
| EC Source | None | |
| Stop Condition | ARC Stop | |
| IC Inlet Rate (mL/min) | Default: 50 | |
| | Range: 20 to 100 mL/min | |
| IC Circulation Rate (mL/min) | Default: $V_{ICL}/\text{min} - Q_{ICA}$ | |
| | Range: 20 to 300 mL/min | |
| EC Inlet Rate (mL/min) | Default: 0 | |
| EC Circulation Rate (mL/min) | Default: $Q_{ECCM}$ | |
| | Range: 10 to 300 mL/min | |
| Outlet | EC Waste | |
| Rocker Control | On (−90°, 180°, 1 sec) (Def) | Range: Full Range (deg, time) |
| | Fixed (0°) | Range: full range (deg) |
| Output: IC volume | rate as defined by Stop Condition | |
| Output: EC volume | N/A | |
| Output: Remaining time of step | ARC stop as defined by Stop Condition | |

Note:
$Q_{ICA}t + Q_{ICC}t = nV_{ICL}$

Step 2: ARC Chase

Purpose of Step: Chases the cells from the ARC into the IC loop.

Precondition: Fill ARC

| | Input Range |
|---|---|
| IC Source | Reagent |
| | IC Media (Default) |
| | Wash |
| | EC Media |
| EC Source | None |
| Stop Condition | IC volume: $(V_{ARCA} + V_{ARCBS}) * 2$ |
| | Range: 1 to 100 |
| IC Inlet Rate (mL/min) | Default: Same as Step 1 |
| IC Circulation Rate (mL/min) | Default: Same as Step 1 |
| EC Inlet Rate (mL/min) | Default: 0 |
| EC Circulation Rate (mL/min) | Default: Same as Step 1 |
| Outlet | EC Waste |
| Rocker Control | Same as Step 1 |
| Output: IC volume | Volume as defined by Stop Condition |
| Output: EC volume | N/A |
| Output: Remaining time of step | Countdown in minutes or manual stop as defined by Stop Condition |

Step 3: Load Bioreactor

Purpose of Step: Chases the cells from the IC loop into the bioreactor.

| | Input Range |
|---|---|
| IC Source | Reagent |
| | IC Media (Default) |
| | Wash |
| | EC Media |

-continued

| | Input Range |
|---|---|
| EC Source | None |
| Stop Condition | IC volume: 1.5 × $V_{EF}$ (Default) |
| | Range: $0.5V_{EF}$ to $2.0V_{EF}$ |
| IC Inlet Rate (mL/min) | Default: Same as Step 1 |
| IC Circulation Rate (mL/min) | Default: $-V_{ABO}$ % of $Q_{ICA}$ |
| EC Inlet Rate (mL/min) | Default: 0 |
| EC Circulation Rate (mL/min) | Default: Same as Step 1 |
| Outlet | EC Waste |
| Rocker Control | Same as Step 1 |
| Output: IC volume | Volume as defined by Stop Condition |
| Output: EC volume | N/A |
| Output: Remaining time of step | Countdown in minutes as defined by Stop Condition |

Protocol 3: Bone Marrow Washout Example

In an embodiment, this protocol is to remove non-attached/non-adhered cells from the bioreactor. It is for 25 mL to 62 mL bone marrow load though it could be used for load above 10 mL. The bone marrow washout generally follows bone marrow load. It can also be a wash out protocol when the bioreactor is packed with a large number of cells though this protocol is typically done after an initial load. The types of cells removed include red blood cells, platelets and non-adherent bone marrow cells.

The protocol includes the following:

1) IC media introduced through valve 250. This may be approximately 500 mL with protein. Optionally wash or EC media could be introduced.

2) EC media is generally media without protein introduced through valve 276. Optionally wash or IC media could be introduced on EC side.

3) IC inlet rate (mL/min) through pump 254 is expressed as follows:

$$= \begin{vmatrix} 0, & 0 < t < t_1 \\ 20 + ((Q/2) - 20) \times ((t - t_1)/t_1), & t_1 < t \leq t_2 \\ (Q/2) + (Q/2) \times ((t - t_2)/(t_3 - t_2)), & t_2 < t \leq t_3 \\ 0, & t_3 < t \end{vmatrix}$$

In this example the maximum is 100 mL/min.

4) IC circulation rate is expressed as follows: $-AB\% * Q_{ICA}$ $AB\% = V_{AB} * 100/V_{ICL}$ $V_{AB}$=volume from point A to B on FIG. 2

$V_{ICL}$=IC loop volume

5) EC inlet rate (mL/min)

$$= \begin{vmatrix} 20 + ((Q/2) - 20) \times (t/t_1) & 0 < t \leq t_1 \\ Q/2 & t_1 < t \leq t_2 \\ (Q/2) - (Q/2) \times ((t - t_2)/(t_3 - t_2)) & t_2 < t \leq t_3 \\ 0, & t_3 < t \end{vmatrix}$$

6) The parameters for both the IC inlet and EC inlets rates are defined in the table following:

| Parameter | Equation |
|---|---|
| V | User input - Total IC + EC volume to be pumped (mL). |
| Q | User input - Maximum IC inlet rate (mL/min). Q > 40 mL/min. |
| $t_1$ (minutes) | = V × ((2 × (Q − 40)/(3 × $Q^2$ − 40 × Q − 1600)) |
| $t_2$ (minutes) | = 2 × $t_1$; $t_3$ (minutes) = (5/2) × ((Q − 32)/(Q − 40)) × $t_1$ |

7) EC circulation rate (mL/min)=$Q_{ECCM}$ of a range from 10 to 300 mL/min.

$Q_{ECCM}$=rate to keep EC loop well mixed in this example 30 mL/min.

8) Rocker control for bioreactor 100 is on with −90°, 180°, for 1 second pause at the ends.

9) The stop condition in this example is an inlet volume of 1000 mL with a range from 400 to 4000.

10) Maximum flow rate of output washout is 100 mL in range from 80 to 200.

Summary of the protocol is below.

Protocol 3 Bone Marrow Washout

Purpose of protocol: Meant for use following a bone marrow load (25 mL to 62 mL) and attachment phase, this protocol is recommended to remove any non-attached/non-adhered cells from the bioreactor.

This is also a useful washout protocol for any occasion when the bioreactor is packed with a similar large number of cells. For bone marrow loads of 10 mL or less, Protocol Aggressive Washout is recommended. For bone marrow loads between 10 mL to 25 mL, this protocol is optional but may not be required.

Step 1: Bone Marrow Washout

| | Input Range |
|---|---|
| IC Source | IC Media(Default) |
| | Wash |
| | EC Media |
| EC Source | IC Media |
| | Wash |
| | EC Media (Default) |
| Stop Condition | Volume = 1000 Range: 400 to 4000 |
| Washout Parameters | Maximum Flow Rate (MFR) = 100 Range: 80 to 200 |
| IC Inlet Rate (mL/min) | $= \begin{vmatrix} 0, & 0 < t \leq t_1 \\ 20 + ((Q/2) - 20) \times ((t - t_1)/t_1), & t_1 < t \leq t_2 \\ (Q/2) + (Q/2) \times ((t - t_2)/(t_3 - t_2)), & t_2 < t \leq t_3 \\ 0, & t_3 < t \end{vmatrix}$ |
| | where parameters are defined in table following. |
| IC Circulation Rate (mL/min) | Value: −AB% * $Q_{ICA}$ |
| EC Inlet Rate (mL/min) | $= \begin{vmatrix} 20 + ((Q/2) - 20) \times (t - t_1) & 0 < t \leq t_1 \\ Q/2 & t_1 < t \leq t_2 \\ (Q/2) - (Q/2) \times ((t - t_2)/(t_3 - t_2)) & t_2 < t \leq t_3 \\ 0, & t_3 < t \end{vmatrix}$ |
| EC Circulation Rate (mL/min) | Default: $Q_{ECCM}$ Range: 10 to 300 mL/min |
| Outlet | IC Waste |
| Rocker | On (−90°, 180°, 1 sec) Range: full range (deg, time) |
| Output: IC volume | Volume as defined by stop condition |

| | Input Range |
|---|---|
| Output: EC volume | Volume as defined by stop condition |
| Output: Remaining time of step | Countdown in minutes as defined by stop condition |

| Parameter | Equation |
|---|---|
| V | User input - Total IC + EC volume to be pumped (mL). |
| Q | User input - Maximum IC inlet rate (mL/min). Q > 40 mL/min. |

$t_1$ (minutes) = V × ((2 × (Q − 40))/(3 × $Q^2$ − 40 × Q − 1600))
$t_2$ (minutes) = 2 × $t_1$;
$t_3$ (minutes) = (5/2) × ((Q − 32)/(Q − 40)) × $t_1$ Protocol 4: Aggressive Washout for Bone Marrow Loads below 10 mL Example In an embodiment, this protocol produces a small amount ultrafiltration into the hollow fiber of the bioreactor membrane 116 across the entire filter length. The purpose of the protocol is to remove non-adherent cells from the bioreactor.

The protocol includes:

1) IC source is IC media introduced through valve 250 by pump 254. Alternatively the IC source could be reagent, wash, or EC media. The IC media may be media with protein estimated in this example to be about 500 mL.

2) EC source is EC media introduced through valve 276 by pump 278. Alternatively the EC source could be reagent, IC media, or wash. This may be media without protein.

3) IC pump 254 is set at approximately 260 mL/min inlet rate from a range of 50 to 500 mL/min.

4) IC circulation rate is −AB %*$Q_{ICA}$, in this example, −45 mL/min.

5) EC inlet rate is 40 mL/min from a range of 0 to 100 mL/min.

6) EC circulation rate is $Q_{ECCM}$ or the rate to keep the loop well mixed from a range of 10 to 300 mL/min, in this example 30 mL/min.

7) The IC source goes to waste.

8) The rocker control for the bioreactor 100 may be set at −90% to 180% for 1 second pause at the ends of the range of motion or optionally could be fixed.

9) The stop condition for the process may be based on time such as up to 60 minutes; IC volume as defined in the Bone Marrow Washout which may range from is from 0 to 4000 mL range; or the number of IC exchanges or number of times the IC source fluid is circulated. The number of IC exchanges may be 2.5 from a range of 0.5 to 5.0

Summary of the protocol is below.

Protocol 4 Aggressive Washout

Purpose of protocol: Removes non-adherent cells from the bioreactor. This protocol imposes a small ultrafiltration into the fiber across the entire fiber length.

Step 1: Aggressive Washout

| | Input Range |
|---|---|
| IC Source | Reagent |
| | IC Media (Default) |
| | Wash |
| | EC Media |
| EC Source | Reagent |
| | IC Media |
| | Wash |

| | Input Range |
|---|---|
| | EC Media (Default) |
| Stop Condition | Time: (1 min)  Range: 0.1 to 60 min |
| | IC volume: ($V_{ICE}$)  Range: 1 to 4000 mL |
| | # of IC exchanges:  Range 0.5 to 5.0 |
| | 2.5 (default) |
| IC Inlet Rate (mL/min) | Default: 260 |
| | Range: 50 to 500 mL/min |
| IC Circulation Rate (mL/min) | Default: −AB % * $Q_{ICA}$ |
| EC Inlet Rate (mL/min) | Default: 40 |
| | Range: 0 to 100 mL/min |
| EC Circulation Rate (mL/min) | Default: $Q_{ECCM}$ |
| | Range: 10 to 300 mL/min |
| Outlet | IC Waste |
| Rocker Control | On (−90°, 180°,  Range: Full Range |
| | 1 sec) (Def)  (deg, time) |
| | Fixed (0°)  Range: Full range (deg) |
| Output: IC volume | Volume as defined by Stop Condition |
| Output: EC volume | Volume as defined by Stop Condition |
| Output: Remaining time of step | Countdown in minutes as defined by Stop Condition |

Protocol 5: IC or EC Washout Example

In an embodiment, this protocol is to replace media while growing adherent cells. The protocol washes out cellular debris and non-adherent cells. The replacement volume is the number of IC and EC exchanges to be performed or IC or EC volume exchanged.

$V_{ICE}$ (IC exchange volume) equals IC loop volume plus volume from media, reagent or wash bags to IC loop.

$V_{ICE}$ (EC exchange volume) equals EC loop volume plus volume from media, reagent or wash bags to EC loop.

The protocol includes the following.

1) The IC source is IC media introduced through valve 250 by pump 254. Reagent, EC media, or wash solution may optionally be used. The IC media may be media with protein. In this example the volume may be at least 550 mL.

2) The EC source is EC media introduced through valve 276 by pump 278. Reagent, IC media, or wash solution may optionally be used. The EC media may be media without protein. In this example the volume may be at least 810 mL 3) The IC inlet rate is $Q_{ECA}$ (number of IC Exc*$V_{ICE}$)/(number of EC Exc*$V_{ICE}$)

$Q_{ECA}$=EC inlet pump rate $V_{ICE}$=IC exchange volume which in this example is 218.4 mL.

$V_{ICE}$=EC exchange volume which in this example is 324.1 mL.

4) IC circulation rate is −AB %*$Q_{ICA}$

AB %=$V_{AB}$ (volume from point A to B in FIG. 2)*100/$V_{ICL}$. $V_{ICL}$ is IC loop volume.

$Q_{ICA}$=IC inlet pump 254 rate

5) The EC inlet rate is the lesser of $Q_{100}$ or $Q_{MAX}$ where $Q_{100}$=100 (number of EC Exc*$V_{ECE}$)/(number of IC Exc*$V_{ICE}$) and $Q_{MAX}$=300

6) The EC circulation rate is −CD %*$Q_{ECA}$. CD %=$V_{CD}$ (or volume from point C to D, in this example 3.8 mL)*100/$V_{ECE}$.

7) The outlet for the media or washout fluid is either the IC, EC, or both waste 286.

8) The rocker control for the bioreactor 100 is −90° to 180° with 1 second pause at the end of the range of motion. Or alternatively, there is no rocker control motion.

9) The stop condition to end the process includes the number of IC exchanges (Exc.) which may be 2.5 or optionally within a range from 0.5 to 5. The stop condition also includes the number of EC exchanges which may be 2.5 or optionally within a range from 0.5 to 5.

A summary of this protocol is as follows.

Protocol 5 IC or EC Washout

Purpose of protocol: Meant for use when growing adherent cells to replace the media in both the IC loop and EC loop. This protocol provides some washout of cellular debris and non-adherent cells. The replacement volume is specified as the number of IC and EC exchanges to be performed.

Calculations:
One IC exchange volume ($V_{ICE}$) is equal to the IC Loop Volume plus the volume from bags to IC loop.
One EC exchange ($V_{ECE}$) is equal to the EC Loop Volume plus the volume from bags to EC Loop.

Step 1: Washout

| | Input Range |
|---|---|
| IC Source | Reagent |
| | IC Media (Default) |
| | Wash |
| | EC Media |
| EC Source | Reagent |
| | IC Media |
| | Wash |
| | EC Media (Default) |
| Stop Condition | # of IC Exchanges: 2.5 (default) range: 0.5-5.0 |
| | # of EC Exchanges: 2.5 (default) range: 0.5-5.0 |
| IC Inlet Rate (ml/min) | Value: $Q_{ECA}$ (# of IC Exc. * $V_{ICE}$)/ (# of EC Exc. * $V_{ECE}$) |
| IC Circulation Rate (ml/min) | Value: $-AB\% * Q_{ICA}$ |
| EC Inlet Rate (ml/min) | Initial value: the lesser of $Q_{100}$ or $Q_{max}$; where $Q_{100} = 100$ (# of EC Exc. * $V_{ECE}$)/ (# of IC Exc. * $V_{ICE}$) and $Q_{max} = 300$. |
| EC Circulation Rate (ml/min) | Value: $-CD\% * Q_{ECA}$ |
| Outlet | EC Waste |
| | IC Waste |
| | IC&EC Waste (default) |
| Rocker Control | On (−90°, 180°, Range: full range |
| | 1 sec) (Def) (deg, time) |
| | Fixed (0°) Range: Full range (deg) |
| Output: IC volume | Volume as defined by Stop Condition |
| Output: EC volume | Volume as defined by Stop Condition |
| Output: Remaining time of step | Countdown in minutes as defined by Stop Condition |

Protocol 6: Washout through the Membrane Example

In an embodiment, this protocol is to move small molecular components on the IC side to the EC side of the membrane 116. These molecules pass through the membrane by diffusion or ultrafiltration. These could include bi-products of the cell growth. IC components retained by the membrane are not removed from the IC loop. The small molecular weight elements are washed out of the EC side by replacement fluid.

The replacement volume is specified by the number of IC volumes–EC volumes exchanged.

The protocol includes:
1) The introduction of IC media or optionally other media to the IC side. This may be media with protein.
2) The introduction of EC media or optionally other media to the EC side. This may be media without protein.
3) The IC inlet rate as described for IC/EC washout.
$Q_{ECA}$(number of IC Exc*$V_{ICE}$)/(number of EC Exc*$V_{ECE}$)
4) The IC circulation rate is defined by $-V_{ABO}\%*Q_{ICA}$.
$V_{ABO}\%=V_{ABO}*10/V_{ABI}+V_{ABO}$
$V_{ABO}$ is from point A to bioreactor outlet F on FIG. 2 and in this example is 42.1 mL.

$V_{ABI}$ is from point A to bioreactor inlet E on FIG. 2 and in this example is 9 mL.

5) The EC inlet rate is the lesser of $Q_{65}$ or $Q_{MAX}$ where $Q_{65}$ is defined the same as $Q_{100}$ for IC/EC washout above.

6) The EC circulation rate is $-CD\%*Q_{ECA}$ as described above for IC/EC washout.

7) The outlet is EC waste.

8) The rocker control is the same for IC/EC washout.

9) The stop condition is the number of IC and EC exchanges which may be 1 or within the range of 0.5 to 5.

The brief summary is as follows.

Protocol 6 IC/EC Washout through Membrane

Purpose of protocol: Replaces small molecule components on IC side, which pass through the membrane by either diffusion or by ultra filtration. IC components retained by the membrane are not removed from the IC loop. Components on EC side are washed out by fluid replacement. The replacement volume is specified as the number of IC and EC exchanges to be performed.

Calculations:
One IC exchange volume ($V_{ICE}$) is equal to the IC Loop Volume plus the volume from bags to IC loop.
One EC exchange ($V_{ICE}$) is equal to the EC Loop Volume plus the volume from bags to EC Loop.

Step 1: Washout through Membrane

| | Input Range |
|---|---|
| IC Source | Reagent |
| | IC Media (Default) |
| | Wash |
| | EC Media |
| EC Source | Reagent |
| | IC Media |
| | Wash |
| | EC Media (Default) |
| Stop Condition | # of IC Exchanges: 1 (default) range: 0.5-5.0 |
| | # of EC Exchanges: 1 (default) range: 0.5-5.0 |
| IC Inlet Rate (ml/min) | Value: $Q_{ECA}$ (# of IC Exc. * $V_{ICE}$)/ (# of EC Exc. * $V_{ECE}$) |
| IC Circulation Rate (ml/min) | Value: $-V_{ABO}\% * Q_{ICA}$ |
| EC Inlet Rate (ml/min) | Initial value: the lesser of $Q_{65}$ or $Q_{max}$; where $Q_{65} = 100$ (# of EC Exc. * $V_{ECE}$)/ (# of IC Exc. * $V_{ICE}$) and $Q_{max} = 300$. |
| EC Circulation Rate (ml/min) | Value: $-CD\% * Q_{ECA}$ |
| Outlet | EC Waste |
| Rocker | On (−90°, 180°, Range: full range |
| | 1 sec) (def) (deg, time) |
| | fixed(0°) Range: full range (deg) |
| Output: IC volume | Volume as defined by Stop Condition |
| Output: EC volume | Volume as defined by Stop Condition |
| Output: Remaining time of step | Countdown in minutes as defined by Stop Condition |

Protocol 7: Continuous Add of IC with Ultrafiltration Example

In an embodiment, this protocol adds generally IC fluid at a low flow rate and keeps large molecules on the IC side of the fiber. A similar protocol could be used to add fluid at low flow rate to the EC side. Excess IC fluid will be removed through ultrafiltration if the IC inlet pump 254 is used.

This Protocol Includes:
1) The IC media is introduced through valve 250 by pump 254 with other media being optional alternatives.
2) EC media may optionally be added but in the IC example the EC inlet flow rate is 0.
3) The IC inlet flow rate is 0.1 mL/min from a range of 0 to 10 mL/min.

4) The IC circulation rate through IC loop 202 is at a maximum of $Q_{ICCM}$, $10 \times Q_{ICA}$.

$Q_{ICCM}$ is the IC circulation pump rate to keep IC loop 202 well mixed without preventing air from entering filter 116. The inlet pump 254 rate $Q_{ICA}$ plus the circulation pump 212 rate equals the $Q_{ICCM}$ which in this example is 20 mL/min.

5) The EC circulation rate is $Q_{ECCM}$ or the pump 228 rate to keep the EC loop 204 well mixed, for example 30 mL/min.

6) The outlet for the excess IC fluid is EC waste as the fluid enters the EC loop 204 through ultrafiltration through the membrane.

7) The rocker control for bioreactor 100 is fixed.

8) The stop condition is a manual stop by the operator although alternatively the stop could be based on selected time or selected IC or EC volume.

Below is a summary of the Continuous Add with Ultrafiltration protocol.

Protocol 7 Continuous Add with Ultra Filtration

Purpose of protocol: Continuously adds fluid at a low flow rate to the IC loop and/or the EC loop. Large molecules may be concentrated in the IC loop if you use the IC Inlet pump for this task. This protocol uses ultrafiltration to remove excess IC fluid if you use the IC Inlet pump.

Step 1: Feed

| | Input Range |
|---|---|
| IC Source | Cell Inlet |
| | Reagent |
| | IC Media (Default) |
| | Wash |
| | EC Media |
| | None |
| EC Source | Reagent |
| | IC Media |
| | Wash |
| | EC Media (Default) |
| | None |
| Stop Condition | Time (1440 min)  Range: 0.1 to 1440 minutes |
| | Manual Stop (Default) |
| | IC volume: (150 mL)  Range: 1 to 4000 mL |
| | EC volume: (150 mL)  Range: 1 to 4000 mL |
| IC Inlet Rate (ml/min) | Default: 0.1 |
| | Range: 0 to 10 mL/min |
| IC Circulation Rate (ml/min) | Default: Maximum of ($Q_{ICCM}$, $10 \times Q_{ICA}$) |
| | Range: −100 to 100 mL/min |
| EC Inlet Rate (ml/min) | Default: 0 |
| | Range: 0 to 10 mL/min |
| EC Circulation Rate (ml/min) | Default: $Q_{ECCM}$ |
| | Range: 10 to 300 mL/min |
| Outlet | EC Waste |
| Rocker Control | On (−90°, 180°, 1 sec)  Range: full range (deg, time) |
| | Fixed (0°) (Def)  Range: full range (deg) |
| Output: IC volume | Volume or rate as defined by Stop Condition |
| Output: EC volume | Volume or rate as defined by Stop Condition |
| Output: Remaining time of step | Countdown in minutes or manual stop as defined by Stop Condition |

Protocol 8: Continuous Add with Active Removal Example

In an embodiment, this protocol uses a relatively low flow rate to continuously add to the IC and/or EC loops. Excess IC fluid is removed using EC waste through the membrane 116.

The protocol includes:

1) IC media is added through valve 250 and pump 254 to the IC circuit. Alternatively, other media could be provided continuously such as cell inlet, reagent, wash solution or EC media. If the addition of media or fluid is only for the EC side, there may be no input of fluid through the IC side.

2) Optionally or alternatively media may be added from an EC source to the EC side if only EC addition is desired. The addition may be EC media through valve 276 and pump 278.

Alternatively there may be no EC input as the addition is only to the EC side. Reagent, IC media, or wash solution could also be added to the EC side.

3) On the IC side the IC inlet rate of pump 254 is 0.1 mL/min for low flow rate addition. This is selected from a range of 0 to 10 mL/min.

4) For IC addition the IC circulation rate is the maximum of $Q_{ICCM}$ or $10 \times Q_{ICA}$ with $Q_{ICCM}$ being the rate of the IC circulation pump 212 to keep the IC loop well mixed and $Q_{ICA}$ being the rate of the inlet pump 254 in mL/min selected from a range from −100 to 100 mL/min. For example it may be 20 mL/min.

5) If the low flow addition is to the EC side the EC inlet rate may be selected to be 0.1 mL/min from a range of 0 to 20 mL/min.

6) For the EC addition the EC circulation rate is selected to be $Q_{ECCM}$ which is the rate of the circulation pump 228 in mL/min selected from a potential range of 0 to 100 mL/min, for example 30 mL/min.

7) The outlet in this example is EC waste.

8) The rocker control for the bioreactor 100 is off with no rotation.

9) The stop condition for the protocol is manually though it alternatively may be based on the time (for example 0.1 to 1440 minutes) or IC or EC volumes (for example IC or EC volumes may be from 1 to 4000 mL).

The brief summary of this protocol is set forth below.

Protocol 8 Continuous Add with Active Removal

Purpose of protocol: Continually adds a low flow rate to the IC and/or EC loops. A pump is used to remove excess IC fluid.

Step 1:

| | Input Range |
|---|---|
| IC Source | Cell Inlet |
| | Reagent |
| | IC Media (Default) |
| | Wash |
| | EC Media |
| | None |
| EC Source | Reagent |
| | IC Media |
| | Wash |
| | EC Media (Default) |
| | None |
| Stop Condition | Time |
| | Manual Stop (Default) |
| | IC volume: |
| | EC volume: |
| IC Inlet Rate (ml/min) | Default: 0.1 |
| | Range: 0 to 10 mL/min |
| IC Circulation Rate (ml/min) | Default: Maximum of ($Q_{ICCM}$, $10 \times Q_{ICA}$) |
| | Range: −100 to 100 mL/min |
| EC Inlet Rate (ml/min) | Default: 0.1 |
| | Range: 0 to 20 mL/min |
| EC Circulation Rate (ml/min) | Default: $Q_{ECCM}$ |
| | Range: 0 to 100 mL/min |
| Distribution Rate (ml/min) | Default: = (—) $Q_{ICA}$ |
| Outlet | EC Waste (Default) |
| Rocker Control | On |
| | Off (Default) |
| | fixed |
| Output: IC volume | Volume or rate as defined by Stop Condition |
| Output: EC volume | Volume or rate as defined by Stop Condition |
| Output: Remaining time of step | Countdown in minutes or manual stop as defined by Stop Condition |

Protocol 9: Reagent Add Example

In an embodiment, this protocol loads reagent from reagent bag 244 through valve 248 by pump 254 into the IC side until the bag is empty. The IC waste valve 290 is closed for circulation through circulation loop 202. The cell inlet bag 262 includes at $V_{FTO}$ of air which is defined as $(1+LP\%/100)*V_{ICBL}+5$ mL, for example 38 ml. LP % is about a 20% pump error. $V_{ICBL}$ is the volume from bag 244 to IC loop. The cell inlet bag has at least 10 mL of fluid.

The protocol includes:

1) Introduction of reagent through valve 248 by pump 254 to the IC loop 202.

2) Introduction of air, as pump 254 continues, from cell inlet bag 262.

3) Nothing is introduced on the EC side.

4) The IC inlet rate from pump 254 is 10 mL/min selected from a range of 0 to 100 mL/min.

5) The IC circulation rate from pump 212 is the maximum of the IC circulation pump rate 212 to keep the IC loop 202 well mixed or a value selected from the minimum of 300 or $10 \times Q_{ICA}$ (IC inlet pump 254 rate), for example, 100 mL/min.

6) There is no EC inlet but the circulation rate is the rate of the circulation pump 228 to keep the EC loop well mixed, for example 30 mL/min.

7) The outlet is EC waste through valve 292. IC waste through valve 290 is an option.

8) The rocker control for the bioreactor 100 is fixed or stationary. Alternatively, the rocker control range of motion is from −90° to 180° with 1 second pauses at the end of the motion range.

9) The stop for the reagent load is when air reaches the lower sensor 1264 of the air removal chamber or ARC.

10) After air detection the ARC is filled to the upper sensor 1268 from the IC media or a bag such as wash solution or EC media bag that did not contain reagent. Valve 260 and vent are open to purge ARC air.

11) Media such as IC media through valve 250 and moved by pump 254 continues to chase any reagent from the ARC to the IC loop 202.

12) The stop condition for the chase of reagent is the IC volume $(V_{ARCA}+V_{ARCBS})*2$.

$V_{ARCA}$ is the volume from the bottom sensor of the ARC to point A on FIG. 2.

$V_{ARCBS}$ is the volume of the ARC between top and bottom sensors. For example, the IC volume may be 22 mL. The range for this volume is between 0 to 100 mL.

The brief summary of this protocol is set forth below.

Protocol 9 Reagent Add

Purpose of protocol: Loads reagent from the reagent bag into the IC loop until the bag is empty.

The IC waste valve is closed during this protocol.

Step 1: Load Reagent

Purpose of Step: Loads reagent into the system.

Precondition: Need at least $V_{FTO}$ of air in cell inlet bag.

| | Input Range |
|---|---|
| IC Source | Cell Inlet<br>Reagent (Default) |
| EC Source | None |
| Stop Condition | ARC Stop |
| IC Inlet Rate (ml/min) | Default: 10<br>Range: 0 to 100 mL/min |
| IC Circulation Rate (ml/min) | Default: Maximum of ($Q_{ICCM}$, min(300, 10 × $Q_{ICA}$))<br>Range: −300 to 300 mL/min |
| EC Inlet Rate (ml/min) | Default: 0 |
| EC Circulation Rate (ml/min) | Default: $Q_{ECCM}$<br>Range: 0 to 300 mL/min |
| Outlet | EC Waste (default)<br>IC Waste |
| Rocker Control | On (−90°, 180°, 1 sec) Range: full range (deg, time)<br>Fixed (0°) (Default) Range: full range (deg) |
| Output: IC volume | rate as defined by Stop Condition |
| Output: EC volume | N/A |
| Output: Remaining time of step | ARC Stop as defined by Stop Condition |

Step 2: ARC Chase

Purpose of Step: Chases reagent from the ARC into the IC Loop.

| | Input Range |
|---|---|
| IC Source | IC Media (Default)<br>Wash<br>EC Media<br>Note: user cannot choose same bag used in step 1 because that bag is now empty |
| EC Source | None |
| Stop Condition | IC volume: ($V_{ARCA}$ + $V_{ARCBS}$) * 2<br>Range: 1 to 100 mL |
| IC Inlet Rate (ml/min) | Default: Same as Step 1 |
| IC Circulation Rate (ml/min) | Default: Same as Step 1 |
| EC Inlet Rate (ml/min) | Default: same as Step 1 |
| EC Circulation Rate (ml/min) | Same as Step 1 |
| Outlet | Same as step 1 |
| Rocker | Same as Step 1 |
| Output: IC volume | Volume as defined by Stop Condition |
| Output: EC volume | Volume as defined by Stop Condition |
| Output: Remaining time of step | Countdown in minutes as defined by Stop Condition |

Protocol 10: Bolus Add Example

In an embodiment, this protocol adds a selected volume of reagent into the IC loop. A bolus into the EC loop can also optionally be added. If the IC waste (valve 290) is closed ultrafiltration through the membrane 116 to the EC side will occur.

The protocol includes:

1) Reagent as the IC source is introduced through the pump 254. Alternatively other sources of media or wash could be used for a bolus amount.

2) No EC source. However, if bolus amount is to EC side only there would be no IC source and bolus amount would be introduced by pump 278.

3) For IC bolus, inlet would be 10 mL/min selected from a range up to the rate of the inlet pump.

4) The IC circulation rate is the maximum of $Q_{ICCM}$ as compared to the minimum of 300 or $10 \times Q_{ICA}$ as described above with respect to the Reagent Add protocol. This is selected from the range of −300 to 300 mL/min. In this example it may be 100 mL/min.

5) If the bolus is to the EC side there is no IC inlet or source.

6) The EC circulation is $Q_{ECCM}$ or the rate of the circulation pump 228 to keep the EC loop 204 well mixed. In this example it may be 30 mL/min.

7) The outlet is EC waste through valve 292. Alternatively it could be to harvest through valve 298 or to IC waste through valve 290.

8) The rocker control is off or alternatively could be set for rotation as described previously.

9) The stop condition can be selected to be based on time up to 20 minutes or an IC volume selected to be 10 mL in a range up to 200 mL.

The Bolus Add protocol is summarized below.

Protocol 10 Bolus Add

Purpose of protocol: Quickly adds a selected volume of reagent into the IC loop; you can add an EC bolus at the same time. During the default condition the IC waste valve closed, which forces ultrafiltration.

Step 1: Bolus Add

| | Input Range | |
|---|---|---|
| IC Source | Reagent (Default) | |
| | IC Media | |
| | Wash | |
| | EC Media | |
| | None | |
| EC Source | Reagent | |
| | IC Media | |
| | Wash | |
| | EC Media | |
| | None (Default) | |
| Stop Condition | Time (1 min) | Range: 0.1 to 20 min |
| | IC volume: 10 (Default) | Range: 1 to 200 mL |
| | EC volume: (15 mL) | Range: 1 to 300 mL |
| IC Inlet Rate (ml/min) | Default: 10 | |
| | Range: 0 to $Q_{ARC}$ mL/min | |
| IC Circulation Rate (ml/min) | Default: Maximum of ($Q_{ICCM}$, min(300, 10 × $Q_{ICA}$)) | |
| | Range: −300 to 300 mL/min | |
| EC Inlet Rate (ml/min) | Default: 0 | |
| | Range: 0 to 300 mL/min | |
| EC Circulation Rate (ml/min) | Default: $Q_{ECCM}$ | |
| | Range: 0 to 300 mL/min | |
| Outlet | EC Waste (default) | |
| | IC Waste | |
| | Harvest | |
| Rocker | On (−90°, 180°, 1 sec) | Range: full range (deg, time) |
| | Fixed (0°) (Default) | Range: full range (deg) |
| Output: IC volume | Volume as defined by Stop Condition | |
| Output: EC volume | Volume as defined by Stop Condition | |
| Output: Remaining time of step | Countdown in minutes as defined by Stop Condition | |

Protocol 11: Harvest Cells Example

In an embodiment, this protocol relates to transferring cells once they are in suspension from the IC loop. Additional protocols described below relate to releasing the cells from the membrane 116 in the bioreactor to place them in suspension prior to harvest.

The protocol includes as follows:

1) Media is inputted from an IC source such as IC media through valve 250 and pump 254. Alternatively reagent, wash solution or EC media could be the IC source. The media may be harvest media. As the cells are non-adherent and have been reloaded from the membrane, no tryspin is recirculated after release from the membrane.

2) Similarly EC media is provided through valve 276 and pump 278. Wash solution, reagent or IC media could also be introduced.

3) The IC inlet rate is 400 mL/min selected from a range from 100 to 500 mL.

4) The IC circulation rate is −AB %*$Q_{ICA}$ with AB % is $V_{AB}$*100/$V_{ICL}$. $V_{AB}$ is the volume from point A to point B on FIG. 2 and $V_{ICL}$ is the volume of the IC loop 202. $Q_{ICA}$ is the pump rate of the inlet pump 254. In this example it is 69 mL/min.

5) The EC inlet rate is $UFR_{400}$ or the negative ultrafiltration rate required to have zero transmembrane pressure at the bioreactor outlet in co-current flow and IC inlet rate=400 mL/min and EC waste valve 292 is closed. The upper range is 100 mL/min and in this example it is 60 mL/min.

6) The EC circulation rate is $Q_{ECCM}$ as described previously in a range up to 300 mL/min, for example 30 mL/min.

7) The outlet for the suspended cells is the harvest bag which receives the IC outlet.

8) The rocker control for bioreactor rotation is from −90° to 180° with 1 second pauses at the end position.

9) The stop condition for the protocol is IC volume 2×$V_{ICL}$, for example 378 mL.

The brief summary of the Harvest Cell protocol is as follows.

Protocol 11 Harvest Cells

Purpose of protocol: Transfers cells in suspension from the IC loop, including cells in the bioreactor, to the harvest bag.

Step 1: Harvest Cells

Purpose of Step: Same as Above

| | Input Range |
|---|---|
| IC Source | Reagent |
| | IC Media (Default) |
| | Wash |
| | EC Media |
| EC Source | Reagent |
| | IC Media |
| | Wash |
| | EC Media (Default) |
| Stop Condition | IC volume: 2 × $V_{ICL}$ (Default) |
| | Range: 50 to 1000 mL |
| IC Inlet Rate (ml/min) | Default: 400 |
| | Range: 100 to 500 mL/min |
| IC Circulation Rate (ml/min) | Value = −AB % * $Q_{ICA}$ |
| | Range: −AB % * $Q_{ICA}$ Minimum to −AB % * $Q_{ICA}$ Maximum |
| | Note: $Q_{ICA}$ Minimum and $Q_{ICA}$ Maximum values refer to the IC Inlet Rate (ml/min) Range. |
| EC Inlet Rate (ml/min) | Default: $UFR_{400}$ |
| | Range: 0 to 100 mL/min |
| EC Circulation Rate (ml/min) | Default: $Q_{ECCM}$ |
| | Range: 0 to 300 mL/min |
| Outlet | Harvest |
| Rocker Control | On (−90°, 180°, 1 sec.) (def) |
| | Range: full range (deg, time) |
| Output: IC volume | Volume |
| Output: EC volume | N/A |
| Output: Remaining time of step | Countdown in minutes or manual stop as defined by Stop Condition |

Protocol 12: Release Adherent Cells Example

In an embodiment, this protocol may be executed and followed prior to the Harvest Cell protocol.

The first part of the protocol may include a change of IC/EC media. For example, a media such as PBS may be used to remove protein, calcium or magnesium form the suspension.

The second part of the protocol relates to the addition of a reagent such as trypsin to release the cells from the membrane 116. This is followed by a chase to the IC loop as well as mixing the reagent in the IC loop.

The protocol includes as follows:

1) Addition of wash solution through valve 270, 212 and pump 254 to IC side. Reagent solution, EC media or IC media are optional alternatives if they contain a solution such as PBS. In this example, 1370 mL of PBS was used.

2) If the cells are on the EC side the alternative would be for EC introduction of PBS.

3) The IC inlet rate is $Q_{ECA}$(number of IC Exc*$V_{ICE}$/(number of EC Exc*$V_{ECE}$).

$V_{ICE}$ is the IC exchange volume $V_{ICL}+V^{ICBL}$. $V_{ECE}$ is the EC exchange volume $V_{ECL}+V_{ECBL}$.

4) The IC circulation rate is $-AB\%*Q_{ICA}$ as described in the definitions which in this example is $-17$ mL/min.

5) The EC inlet rate is the lesser of $Q_{100}$ or $Q_{MAX}$ where $Q_{100}=100$ (number of EC Exc*$V_{ICE}$)/(number of IC Exc.*$V_{ICE}$) and $Q_{MAX}=300$. In this example the EC inlet rate is 148 mL/min.

6) The EC circulation rate is $-CD\%*Q_{ECA}$ as defined in the definitions.

7) The outlet can be IC waste or EC waste or both through valves 290 or 292.

8) The rocker control for bioreactor 100 is $-90°$, $180°$ with 1 second pause at the end of the range of motion, or alternatively fixed.

9) The stop condition for the wash is the number of IC and EC exchanges, in this example 2.5 each.

10) The wash is followed by the reagent introduction such as tryspin to release the cells. This is from the reagent bag 244 through valve 248 and pump 254. At least a volume $V_{FTO}$ is needed in the bag.

11) The IC inlet is 50 mL/min.

12) The IC circulation is 300 mL/min.

13) There is no EC inlet but circulation is $Q_{ECCM}$ or rate to keep EC loop mixed.

14) The rocker control is on as described above with chase.

15) The stop condition is the ARC stop or when the lower sensor 1264 detects air.

16) After air detection the ARC is filled with wash or alternatively IC or EC media to upper sensor 1268.

17) Mixing of the reagent continues in the IC loop for 4 minutes.

The protocol summary is as set forth below.

Protocol Release Adherent Cells

Purpose of protocol: Releases cells from the membrane, leaving the cells in the IC Loop.

Step 1:

Purpose of Step: Performs Protocol IC/EC Washout in preparation for adding reagent. For example, the system replaces IC/EC media with PBS to remove protein, $Ca^{++}$, and $Mg^{++}$ in preparation for adding trypsin.

| | Input Range |
|---|---|
| IC Source | Reagent |
| | IC Media |
| | Wash (Default) |
| | EC Media |
| EC Source | Reagent |
| | IC Media |
| | Wash (Default) |
| | EC Media |
| Stop Condition | # of IC Exchanges: 2.5 (default) range: 0.5-5.0 |
| | # of EC Exchanges: 2.5 (default) range: 0.5-5.0 |
| IC Inlet Rate (ml/min) | Value: $Q_{ECA}$ (# of IC Exc. * $V_{ICE}$)/(# of EC Exc. * $V_{ECE}$) |
| IC Circulation Rate (ml/min) | Value: $-AB\% * Q_{ICA}$ |
| EC Inlet Rate (ml/min) | Initial value: the lesser of $Q_{100}$ or $Q_{max}$; where $Q_{100}$ = 100 (# of EC Exc. * $V_{ECE}$)/(# of IC Exc. * $V_{ICE}$) and $Q_{max}$ = 300. |
| EC Circulation Rate (ml/min) | Value: $-CD\% * Q_{ECA}$ |

| | Input Range |
|---|---|
| Outlet | IC Waste |
| | EC Waste |
| | IC&EC Waste (default) |
| Rocker | On (-90°, 180°, 1 sec) Range: full range (def) (deg, time) |
| | Fixed (0°) Range: full range (deg) |
| Output: IC volume | Volume as defined by Stop Condition |
| Output: EC volume | Volume as defined by Stop Condition |
| Output: Remaining time of step | Countdown in minutes as defined by Stop Condition |

Parameters to be Tested:

Check for any updates from Protocol IC/EC Washout.

Step 2: Load Reagent

Purpose of Step: Loads reagent into the system until the bag is empty.

Precondition: Need at least $V_{FTO}$ of air in bag containing the reagent.

| | Input Range |
|---|---|
| IC Source | Cell Inlet |
| | Reagent (Default) |
| EC Source | None |
| Stop Condition | ARC Stop |
| IC Inlet Rate (ml/min) | Default: 50 |
| | Range: 20 to 100 mL/min |
| IC Circulation Rate (ml/min) | Default: 300 |
| | Range: 30 to 300 mL/min |
| EC Inlet Rate (ml/min) | Default: 0 |
| EC Circulation Rate (ml/min) | Default: $Q_{ECCM}$ |
| | Range: 0 to 300 mL/min |
| Outlet | EC Waste |
| Rocker Control | On (-90°, 180°, 1 sec) (def) |
| | Range: full range (deg, time) |
| Output: IC volume | Volume as defined by Stop Condition |
| Output: EC volume | N/A |
| Output: Remaining time of step | ARC Stop as defined by Stop Condition |

Step 3: ARC Chase

Purpose of Step: Chases the reagent into the IC Loop.

| | Input Range |
|---|---|
| IC Source | IC Media |
| | Wash (Default) |
| | EC Media |
| EC Source | None |
| Stop Condition | IC volume: $(V_{ARCA} + V_{ARCBS}) * 2$ |
| | Range: 1 to 100 mL |
| IC Inlet Rate (ml/min) | Default: Same as Step 2 |
| IC Circulation Rate (ml/min) | Default: Same as Step 2 |
| EC Inlet Rate (ml/min) | Default: 0 |
| EC Circulation Rate (ml/min) | Default: Same as Step 2 |
| Outlet | EC Waste |
| Rocker Control | Same as Step 2 |
| Output: IC volume | Volume as defined by Stop Condition |
| Output: EC volume | N/A |
| Output: Remaining time of step | Countdown in minutes as defined by Stop Condition |

Step 4: Mix

Purpose of Step: Mixes the reagent within the IC Loop.

| | Input Range |
|---|---|
| IC Source | None |
| EC Source | None |

| | Input Range |
|---|---|
| Stop Condition | Time: 4 minutes (default) |
| | Range: 0.1 to 20 minutes |
| IC Inlet Rate (ml/min) | Default: 0 |
| IC Circulation Rate (ml/min) | Same as step 2 (default) |
| | Range: 30 to 300 mL/min |
| EC Inlet Rate (ml/min) | Default: 0 |
| EC Circulation Rate (ml/min) | Same as step 2 (default) |
| | Range: 0 to 300 mL/min |
| Outlet | EC Waste |
| Rocker Control | Same as step 2 |
| Output: IC volume | N/A |
| Output: EC volume | N/A |
| Output: Remaining time of step | Countdown in minutes as defined by Stop Condition |

Protocol 13: Condition Media

In an embodiment, this protocol oxygenates the EC media before the addition of cells to the IC side of the bioreactor 100. The initial steps of the protocol include:

1) The EC source is generally EC media without protein introduced through valve 276 by pump 278.

2) IC circulation is enough to prevent air introduction through the hollow fibers or $Q_{ICCM}$. In this example, it is 20 mL/min.

3) The EC inlet rate is 0.1 mL/min.

4) The EC circulation rate is $Q_{ECCE}$ or the pump rate to equilibrate the EC loop. In this example it is 25 mL/min.

5) The outlet is EC waste through valve 292.

6) The rocker control is fixed with no rotation.

7) The stop for the high circulation rate conditioning is based on time from a range of 6 to 15 minutes.

8) A maintenance protocol is part of the condition media protocol.

9) The conditions for maintenance are the same as that outlined above, except that the EC circulation is reduced to $Q_{ECCM}$ which is the rate of the circulation pump to keep the EC loop mixed, for example 30 mL/min. Also, the stop for maintenance is a manual operator controlled stop. The maintenance is maintained until the operator desires cell load.

The summary of the protocol is as follows.

Protocol Condition Media

Purpose of protocol: Oxygenates the media to proper concentrations before loading the cells.

Step 1:

Purpose of Step: Accelerates the conditioning of the media using a high EC circulation rate.

| | Input Range |
|---|---|
| IC Source | None |
| EC Source | Reagent |
| | IC Media |
| | Wash |
| | EC Media (Default) |
| Stop Condition | Time: $T_{CM}$ |
| | Range: 6 to 15 minutes |
| IC Inlet Rate (ml/min) | Default: 0 |
| IC Circulation Rate (ml/min) | Default: $Q_{ICCE}$ |
| EC Inlet Rate (ml/min) | Default: 0.1 |
| EC Circulation Rate (ml/min) | Default: $Q_{ECCE}$ |
| Outlet | EC Waste |
| Rocker | Fixed (0°) |
| | Range: full range (deg) |

| | Input Range |
|---|---|
| Output: IC volume | N/A |
| Output: EC volume | N/A |
| Output: Remaining time of step | Countdown in minutes |

Step 2: Circulate

Purpose of Step: Maintains the system in a proper state until the operator is ready to load the cells.

| | Input Range |
|---|---|
| IC Source | None |
| EC Source | Same as step 1 |
| Stop Condition | Manual Stop |
| IC Inlet Rate (ml/min) | Default: 0 |
| IC Circulation Rate (ml/min) | Same as step 1 |
| EC Inlet Rate (ml/min) | Same as step 1 |
| EC Circulation Rate (ml/min) | Default: $Q_{ECCM}$ |
| | Range: 0 to 100 mL/min |
| Outlet | EC Waste |
| Rocker Control | Fixed (0°) |
| | Range: full range (deg) |
| Output: IC volume | Rate as defined by stop condition |
| Output: EC volume | Rate as defined by stop condition |
| Output: Remaining time of step | manual stop as defined by stop condition |

Protocol 14: Coating Bioreactor Example

In an embodiment, this protocol is directed to coating the IC side of the bioreactor with a reagent such as fibrenectin for cell attachment. Other reagents can be used. The protocol loads the reagent until the reagent bag is emptied, chases the reagent from the ARC, and circulates the reagent. In the protocol, the cell inlet bag contains $V_{FTO}$ or $(1+LP\%/100*V_{IBCL}+5$ mL) as described in the definitions, according to embodiments. In this example, it is 40.2 mL.

The protocol includes:

1) Providing reagent from reagent bag through valve 248 and pump 254 to the IC side.

2) Cell inlet bag also may be open for fluid flow through valve 264.

3) There is no EC source or inlet rate.

4) The IC inlet rate is 10 mL/min.

5) The IC circulation rate is the maximum of (20, (min (300, 10×$Q_{ICA}$)) with $Q_{ICA}$ being the inlet pump 254 rate. In this example, it is 100 mL/min.

6) EC circulation rate is $Q_{ECCM}$ as described previously as the circulation rate to keep to EC loop mixed. In this example, it is 30 mL/min.

7) The outlet is EC waste through valve 292.

8) The rocker control is off. Alternatively it could rotate from −90° to 180° with 1 second pauses at the end of the range of motion.

9) The stop condition for the reagent load is detection of air by lower sensor 1264 of the ARC.

10) After reagent load stop the ARC is loaded to upper sensor 1268 and gas evacuates through outlet 1224 and valve 260.

11) The chase can be IC media, wash or EC media provided through valve 270 if wash solution and pump 254 to the IC side.

12) The stop condition for the chase portion of the protocol is IC volume ($V_{ARCA}$ $V_{ARCBS}$)*2. $V_{ARCA}$ is the volume from the bottom of the ARC to point A on FIG. 2. $V_{ARCBS}$ is the volume of the ARC between sensors.

13) For circulation of the reagent, a low flow EC media is provided on the EC side. This may be media through valve 276 or from the reagent, IC media or wash bags through pump 278.

14) The EC inlet rate during circulation is 0.1 mL/min.

15) The IC inlet rate is $Q_{ICCM}$ which is the circulation pump 212 rate to keep the IC loop well mixed.

16) The EC circulation rate is $Q_{ECCM}$ which is the EC circulation pump 228 to keep the EC loop well mixed, in this example 30 mL/min.

17) The stop condition for circulation is either time selected or a manual stop.

The protocol is summarized below.

Protocol Coat Bioreactor

Purpose of Task: Coats the bioreactor membrane with a reagent.

Step 1: Load Reagent

Purpose of Step: Loads reagent into the system.

Precondition: Need at least $V_{FTO}$ of air in the cell inlet bag.

| | Input Range |
|---|---|
| IC Source | Cell Inlet |
| | Reagent (Default) |
| EC Source | None |
| Stop Condition | ARC Stop |
| IC Inlet Rate (ml/min) | Default: 10 mL/min |
| | Range: 0.1 to 100 mL/min |
| IC Circulation Rate (ml/min) | Default: Maximum of (20, (min(300, 10 × $Q_{ICA}$)) |
| | Range: −300 to 300 mL/min |
| EC Inlet Rate (ml/min) | Default: 0 |
| EC Circulation Rate (ml/min) | Default: $Q_{ECCM}$ |
| | Range: 0 to 100 mL/min |
| Outlet | EC Waste |
| Rocker Control | On (−90°, 180°, 1 sec)  Range: full range (deg, time) |
| | Fixed (0°) (Default)  Range: full range (deg) |
| Output: IC volume | Volume or Rate as defined by stop condition |
| Output: EC volume | Volume or Rate as defined by stop condition |
| Output: Remaining time of step | Countdown in minutes or manual stop as defined by stop condition |

Step 2: ARC Chase

Purpose of Step: Chases reagent from the ARC into the IC Loop.

| | Input Range |
|---|---|
| IC Source | IC Media |
| | Wash (Default) |
| | EC Media |
| EC Source | None |
| Stop Condition | IC volume: ($V_{ARCA}$ + $V_{ARCBS}$) * 2 |
| | Range: 1 to 100 mL |
| IC Inlet Rate (ml/min) | Default: Same as Step 1 |
| IC Circulation Rate (ml/min) | Default: Same as Step 1 |
| EC Inlet Rate (ml/min) | Default: 0 |
| EC Circulation Rate (ml/min) | Default: Same as Step 1 |
| Outlet | EC Waste |
| Rocker Control | Same as Step 1 |
| Output: IC volume | Volume as defined by stop condition |
| Output: EC volume | n/a |
| Output: Remaining time of step | Countdown in minutes or manual stop as defined by stop condition |

Step 3: Circulate

Purpose of Step: Circulates reagent in the IC Loop.

| | Input Range |
|---|---|
| IC Source | None |
| EC Source | Reagent |
| | IC Media |
| | Wash (Default) |
| | EC Media |
| Stop Condition | Time (1 min) |
| | Range: 0.1 to 2880 minutes |
| | Manual Stop (default) |
| IC Inlet Rate (ml/min) | Default: 0 |
| IC Circulation Rate (ml/min) | Default: $Q_{ICCM}$ |
| EC Inlet Rate (ml/min) | Default: 0.1 |
| EC Circulation Rate (ml/min) | Default: $Q_{ECCM}$ |
| Outlet | EC Waste |
| Rocker Control | Same as Step 1 |
| Output: IC volume | n/a |
| Output: EC volume | Rate as defined by stop condition |
| Output: Remaining time of step | Manual stop as defined by stop condition |

Protocol 15: Cell Attachment Example

In an embodiment, the purpose of this protocol is to enable adherent cells to adhere to the IC side of the membrane while allowing flow on the EC side. The cells are already in the IC side.

The protocol includes as follows:

1) Only an EC source and EC circulation is used. There is no IC source, IC inlet rate or IC circulation rate.

2) The EC inlet is EC media with options for reagent, IC media, or wash. The media flows though valve 276 as EC media, and through pump 278.

3) The EC inlet rate is low 0.1 mL/min flow.

4) The EC circulation rate $Q_{ECCM}$ as described above which in this example is 30 mL/min 5) The outlet is the EC waste through valve 290.

6) The rocker control is fixed or stationary.

7) The stop condition is a manual stop. Alternatively the stop could be based on time or EC volume.

The brief summary of the protocol is as shown below.

Protocol Cell Attachment

Purpose of protocol: Enables adherent cells to attach to the membrane while allowing flow on the EC loop. The pump flow rate to the IC loop flow is set to zero.

Step 1: Cell Attachment

| | Input Range | |
|---|---|---|
| IC Source | None | |
| EC Source | Reagent | |
| | IC Media | |
| | Wash | |
| | EC Media (Default) | |
| Stop Condition | Time: (1440 min) | Range: 0.1 to 2880 minutes |
| | Manual Stop (Default) | |
| | EC volume: (150 mL) | Range: 1 to 4000 mL |
| IC Inlet Rate (ml/min) | Default: 0 | |
| IC Circulation Rate (ml/min) | Default: 0 | |
| EC Inlet Rate (ml/min) | Default: 0.1 | |
| | Range: 0.1 to 10 mL/min | |
| EC Circulation Rate (ml/min) | Default: $Q_{ECCM}$ | |
| | Range: 0 to 100 mL/min | |
| Outlet | EC Waste | |
| Rocker Control | Fixed (0°) (Default) | Range: 0° to 180° |
| Output: IC volume | Volume or rate as defined by Stop Condition | |
| Output: EC volume | Volume or rate as defined by Stop Condition | |
| Output: Remaining time of step | Countdown in minutes or manual stop as defined by Stop Condition | |

Protocol 16: User-Defined Task Example

In an embodiment, this protocol allows the user to define the task. The setting options are as follows:

| Setting | Setting Options |
|---|---|
| IC Inlet | Cell |
|  | Reagent |
|  | IC Media |
|  | Wash |
|  | EC Media |
|  | None |
| IC Inlet Rate | 0 to 500 mL/min |
| IC Circulation Rate | −300 to 300 mL/min |
| EC Inlet | Reagent |
|  | IC Media |
|  | Wash |
|  | EC Media |
|  | None |
| EC Circulation Rate | −300 to 300 mL/min |
| Outlet | EC Waste |
|  | IC Waste |
|  | Synchronization |
| Rocker Control | In Motion (−180° to 270°, 0 to 15 seconds) |
|  | Stationary (−180° to 270°) |
| Stop Condition | Manual |
|  | Time (0.1 to 1440 min) |
|  | IC Volume (1 to 4000 mL) |
|  | EC volume (1 to 4000 mL) |

It will be apparent to those skilled in the art that various modifications can be made to the apparatus, systems, and methods described herein. Thus, it should be understood that the embodiments are not limited to the subject matter discussed in the Specification. Rather, the present disclosure is intended to cover modifications, variations, and/or equivalents. The acts, features, structures, and/or media are disclosed as illustrative embodiments for implementation of the claims. The invention is defined by the appended claims.

What is claimed is:

1. A closed cell expansion system comprising a capability to control a process of a protocol, the closed cell expansion system comprising:
    a fluid conveyance assembly, wherein the fluid conveyance assembly comprises a bioreactor;
    an air removal chamber, the air removal chamber comprising a fluid containment chamber, wherein the fluid containment chamber comprises:
        a fluid entrance aperture;
        a fluid exit aperture; and
        a vent aperture;
    at least one sensor for detecting a gas/fluid interface in the fluid containment chamber; and
    a controller, in communication with the at least one sensor, wherein the controller is operable to:
        signal to start a first process of a first protocol, wherein the first protocol comprises loading cells into the bioreactor, wherein the first protocol comprises a first process and a second process, wherein the first process comprises loading the cells into the closed cell expansion system, and wherein a first stop condition for the first process involves the air removal chamber, the signal to start the first process comprising:
            signal to start one or more pumps for pumping a fluid comprising the cells through the fluid entrance aperture and into the fluid containment chamber of the air removal chamber;
        receive an indication from the at least one sensor when the at least one sensor detects the gas/fluid interface;
        in response to receiving the indication from the at least one sensor, determine if the first stop condition for the first process is met;
        when the first stop condition for the first process is met, signal to stop the first process, the signal to stop the first process comprising signal to stop the one or more pumps to stop the first process; and
        signal to start the second process of the first protocol, wherein the second process comprises chasing the cells from the air removal chamber into a circulation loop of the closed cell expansion system, wherein a second stop condition for the second process involves the air removal chamber, and wherein the second stop condition is different from the first stop condition.

2. The closed cell expansion system as defined in claim 1, wherein the at least one sensor comprises an ultrasonic sensor.

3. The closed cell expansion system as defined in claim 1, wherein the first protocol comprises a third process, and wherein the third process comprises chasing the cells from the circulation loop into the bioreactor.

4. The closed cell expansion system as defined in claim 1, wherein the circulation loop comprises an intracapillary loop.

5. The closed cell expansion system as defined in claim 3, wherein the circulation loop comprises an intracapillary loop.

6. The closed cell expansion system as defined in claim 1, wherein the first protocol comprises loading cells into the bioreactor with circulation.

7. The closed cell expansion system as defined in claim 1, wherein the at least one sensor comprises an optical sensor.

8. The closed cell expansion system as defined in claim 1, wherein the controller, in communication with the at least one sensor, is further operable to:
    signal to start a first process of a second protocol, wherein the second protocol is different from the first protocol.

* * * * *